United States Patent
Sanchez et al.

(10) Patent No.: US 11,801,400 B2
(45) Date of Patent: Oct. 31, 2023

(54) THERAPY APPARATUS FOR TREATING TISSUE BY THE EMISSION OF REMOTE CROSSED FOCUSED ULTRASOUND WAVES

(71) Applicants: EDAP TMS FRANCE, Vaulx-en-velin (FR); INSTITUT NATIONAL DE LA SANTE ET DE LA RECHERCHE MEDICALE (INSERM), Paris (FR); UNIVERSITE CLAUDE BERNARD LYON 1, Villeurbanne (FR); CENTRE LEON BERARD, Lyons (FR)

(72) Inventors: Marine Sanchez, Lyons (FR); David Melo De Lima, Saint-Bernard (FR); Jérémy Vincenot, Villeurbanne (FR)

(73) Assignees: EDAP TMS FRANCE, Vaulx-en-Velin (FR); INSTITUT NATIONAL DE LA SANTE ET DE LA RECHERCHE MEDECALE (INSERM), Paris (FR); UNIVERSITE CLAUDE BERNARD LYON 1, Villeurbanne (FR); CENTRE LEON BERARD, Lyons (FR)

( * ) Notice: Subject to any disclaimer, the term of this patent is extended or adjusted under 35 U.S.C. 154(b) by 35 days.

(21) Appl. No.: 17/220,075

(22) Filed: Apr. 1, 2021

(65) Prior Publication Data

US 2021/0308491 A1     Oct. 7, 2021

(30) Foreign Application Priority Data

Apr. 2, 2020   (FR) ...................................... 20 03282

(51) Int. Cl.
*A61N 7/00*     (2006.01)
*A61N 7/02*     (2006.01)

(52) U.S. Cl.
CPC ........ *A61N 7/02* (2013.01); *A61N 2007/0004* (2013.01); *A61N 2007/0065* (2013.01); *A61N 2007/027* (2013.01)

(58) Field of Classification Search
CPC .............. A61N 7/02; A61N 2007/0004; A61N 2007/0065; A61N 2007/027;
(Continued)

(56) References Cited

U.S. PATENT DOCUMENTS 5,522,869 A    6/1996   Burdette et al.
5,643,179 A    7/1997   Fujimoto
(Continued)

FOREIGN PATENT DOCUMENTS

EP          0 214 782 A2     3/1987

OTHER PUBLICATIONS

French Search Report, dated Feb. 5, 2021, corresponding to French Application No. 2003282.
(Continued)

*Primary Examiner* — Christopher Koharski
*Assistant Examiner* — Gabriel Victor Popescu
(74) *Attorney, Agent, or Firm* — LADAS & PARRY LLP; Malcolm J. MacDonald

(57) ABSTRACT

A therapy apparatus for treating tissue by emission of focused ultrasound waves, including: a creation surface of a pressure field of focused ultrasound waves divided into at least N sectors having segments of asymmetrical concave curve with centres of curvature; centres of curvature asymmetrical to the extent where the centres of curvature are situated at different distances from the plane of symmetry or from at least one of the axis of symmetry and at different depths taken according to the axis of symmetry; the individual axes intersecting between the focal zones and the creation surface or beyond the focal zones such that the (Continued)

beams originating from the sectors intersect to create a focal coverage zone which is off-axis relative to the plane of symmetry or to the axis of symmetry; the sectors of this creation surface creating energy deposit zones with profiles corresponding to the focal coverage zones.

15 Claims, 19 Drawing Sheets

(58) Field of Classification Search
CPC .... A61N 2007/0086; A61N 2007/0078; A61N 2007/0095; A61N 7/00; A61N 2007/0073; B06B 2201/76; B06B 1/0207; B06B 1/0633; B06B 1/0637; G10K 11/32; G10K 11/345; G10K 11/346
See application file for complete search history.

(56) References Cited

U.S. PATENT DOCUMENTS

| | | | |
|---|---|---|---|
| 6,506,171 | B1 | 1/2003 | Vitek et al. |
| 9,177,543 | B2* | 11/2015 | Vitek ............... A61N 7/02 |
| 9,737,324 | B2 | 8/2017 | Melodelima et al. |
| 2009/0281463 | A1* | 11/2009 | Chapelon ........... A61N 7/02 |
| | | | 601/2 |
| 2011/0066032 | A1 | 3/2011 | Vitek et al. |
| 2013/0051178 | A1* | 2/2013 | Rybyanets ......... A61N 7/02 |
| | | | 367/138 |
| 2014/0081300 | A1* | 3/2014 | Melodelima ....... A61N 7/02 |
| | | | 606/169 |
| 2015/0112235 | A1 | 4/2015 | Brasset et al. |
| 2018/0050223 | A1 | 2/2018 | Qin |
| 2019/0038922 | A1* | 2/2019 | Carpentier ......... A61N 7/00 |
| 2019/0374205 | A1* | 12/2019 | N'Djin ............... A61N 7/02 |

OTHER PUBLICATIONS

Kennedy, J.E., "High-intensity focused ultrasound in the treatment of solid tumours", Nat Rev Cancer, 2005. 5(4): pp. 321-327.

Aubry, J.F., et al., "The road to clinical use of high-intensity focused ultrasound for liver cancer: technical and clinical consensus", J Ther Ultrasound, 2013. 1: p. 13.

Vincenot, J., et al., "Electronic beam steering used with a toroidal HIFU transducer substantially increases the coagulated volume", Ultrasound Med Biol, 2013. 39(7): pp. 1241-1254.

N'Djin, M. William Apoutou, Ph.D., Thesis, L'Université Claude Bernard Lyon 1, "Transducteur torique à Ultrasons Focalisés de Haute Intensité pour générer des ablations volumineuses, Applications précliniques pour le traitement des métastases hépatiques de cancers colorectaux", Dec. 17, 2008, pp. 1-237.

* cited by examiner

[Fig. 1]
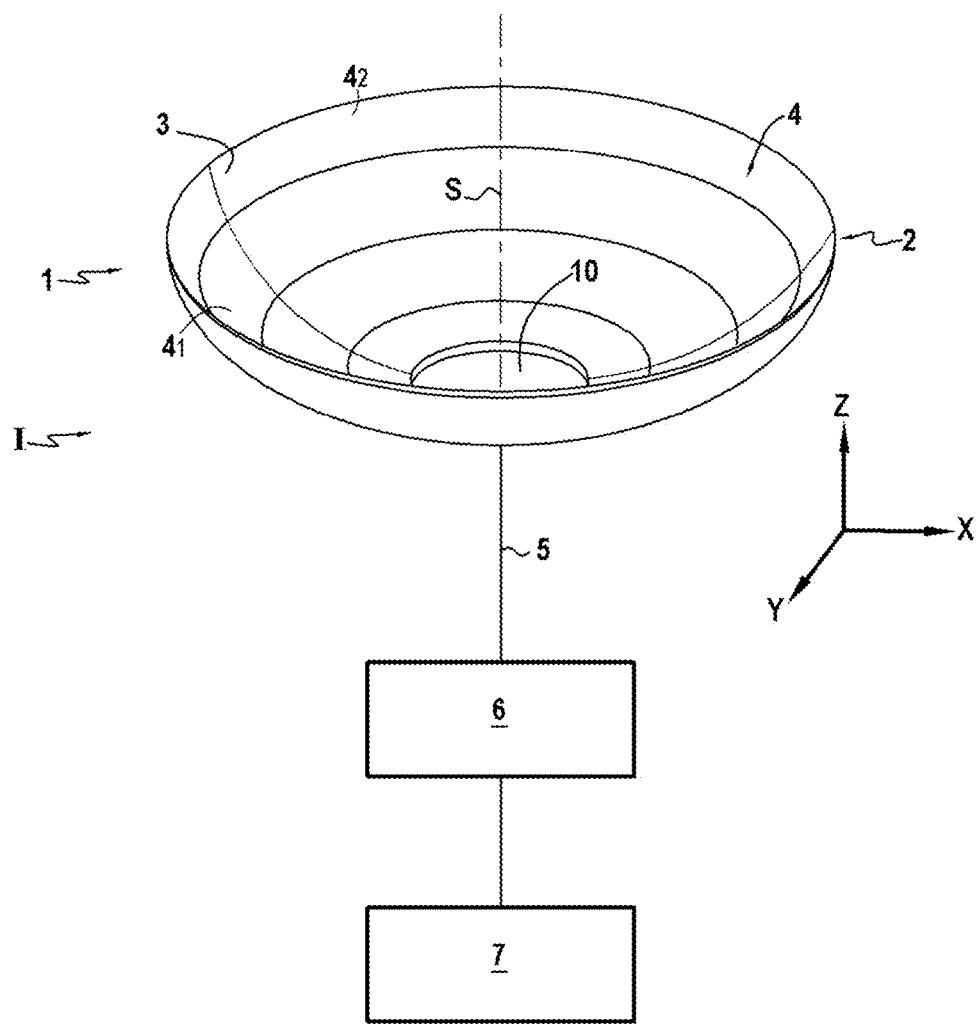

[Fig. 2]
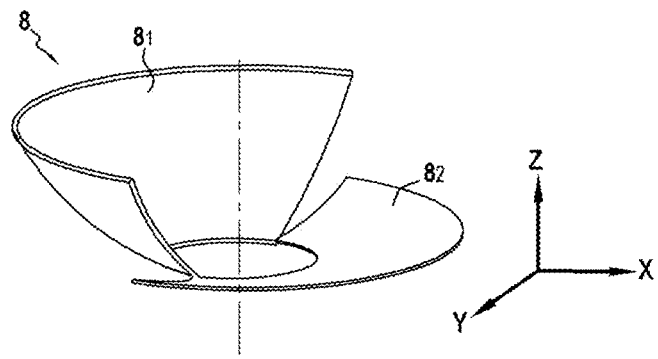
[Fig. 3]
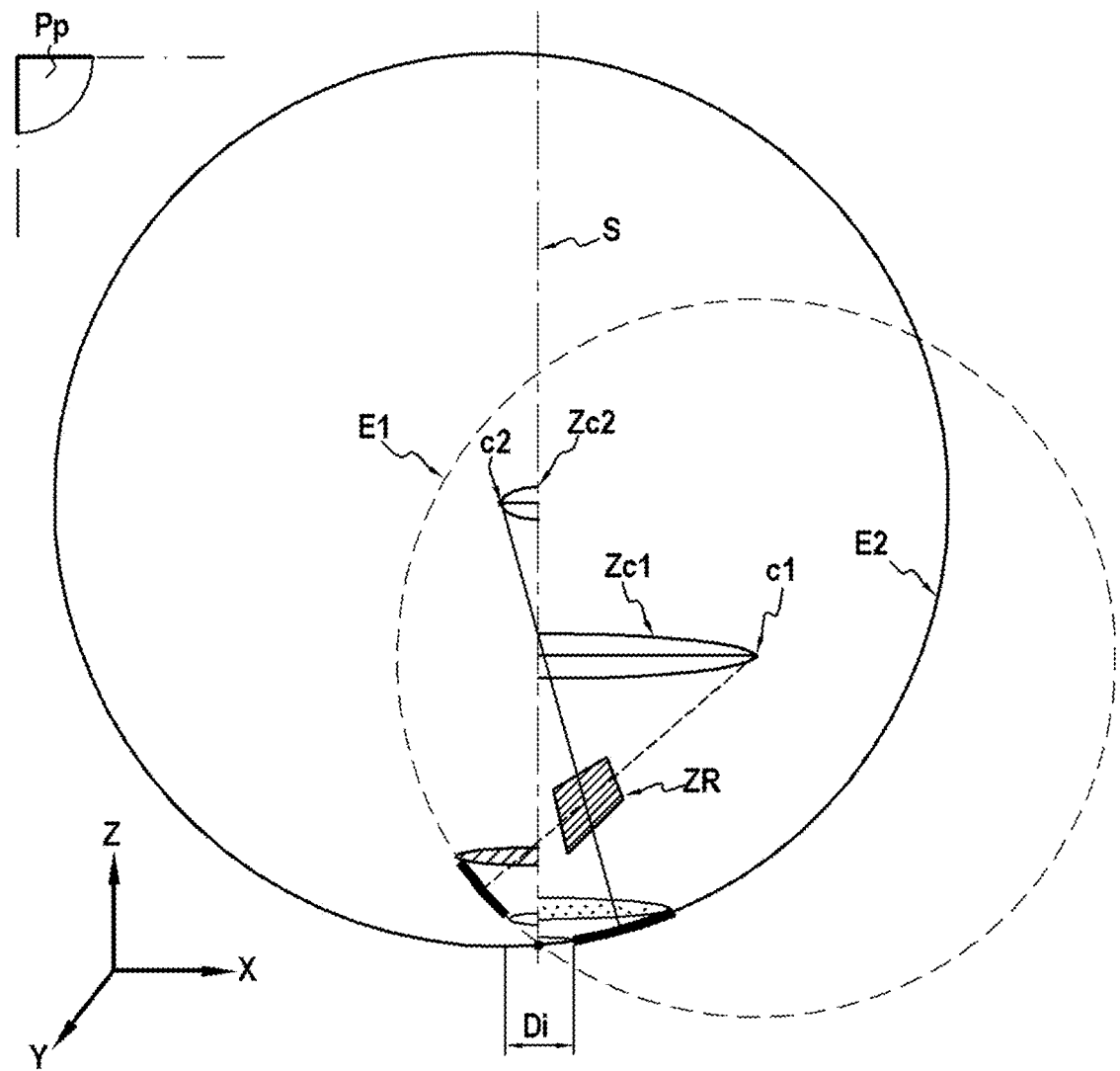

[Fig. 4]
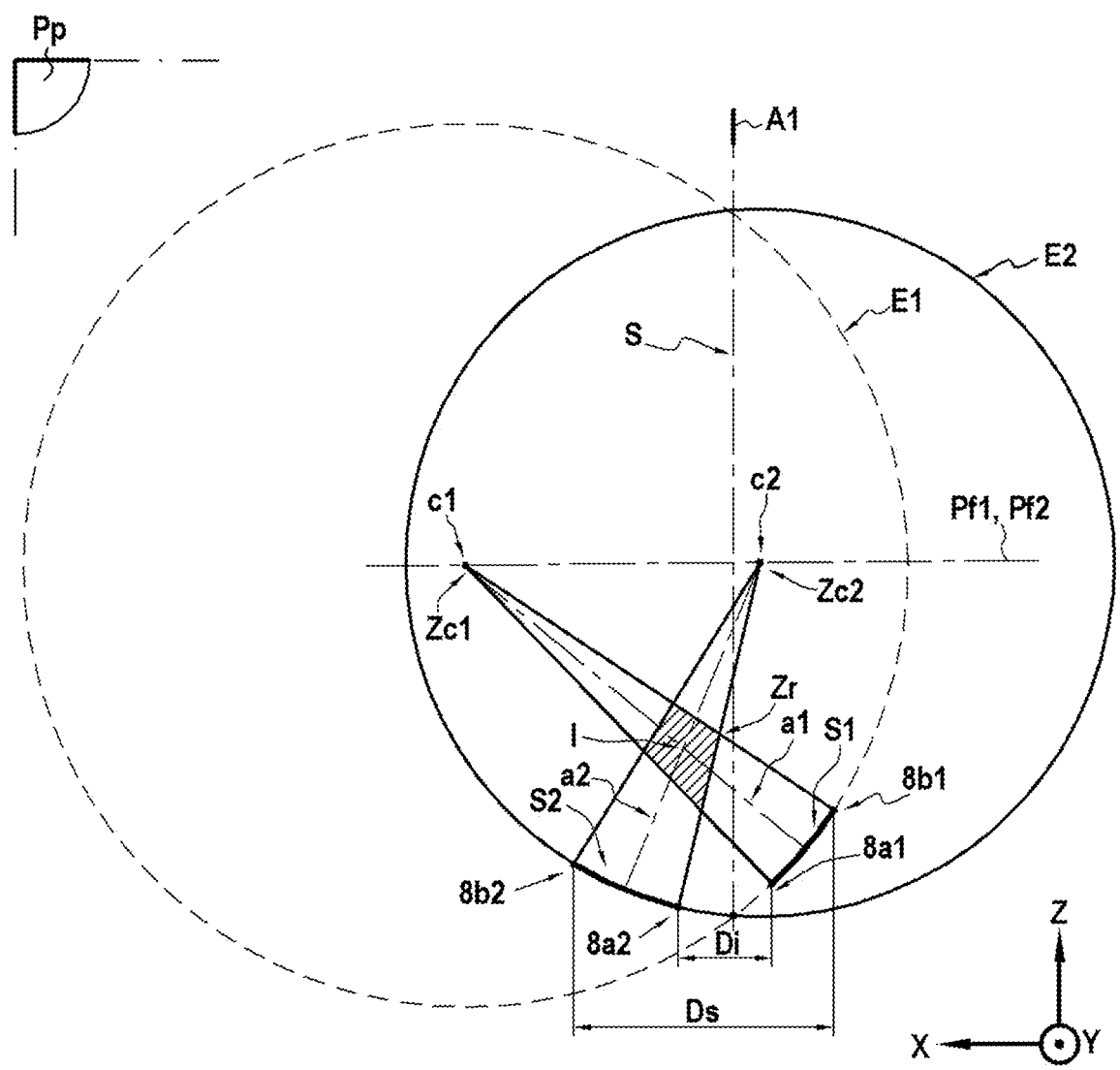

[Fig. 5]
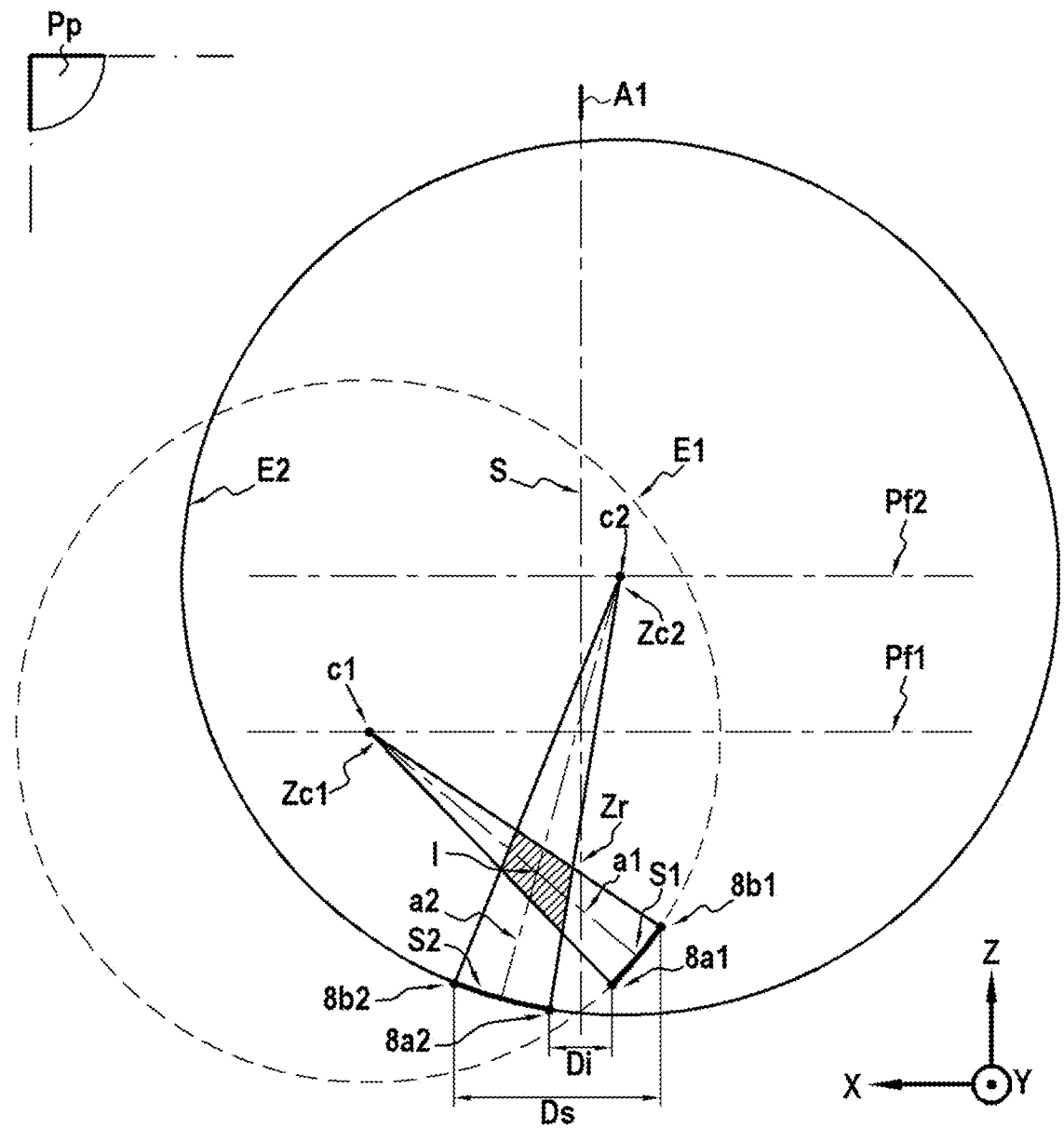

[Fig. 6]
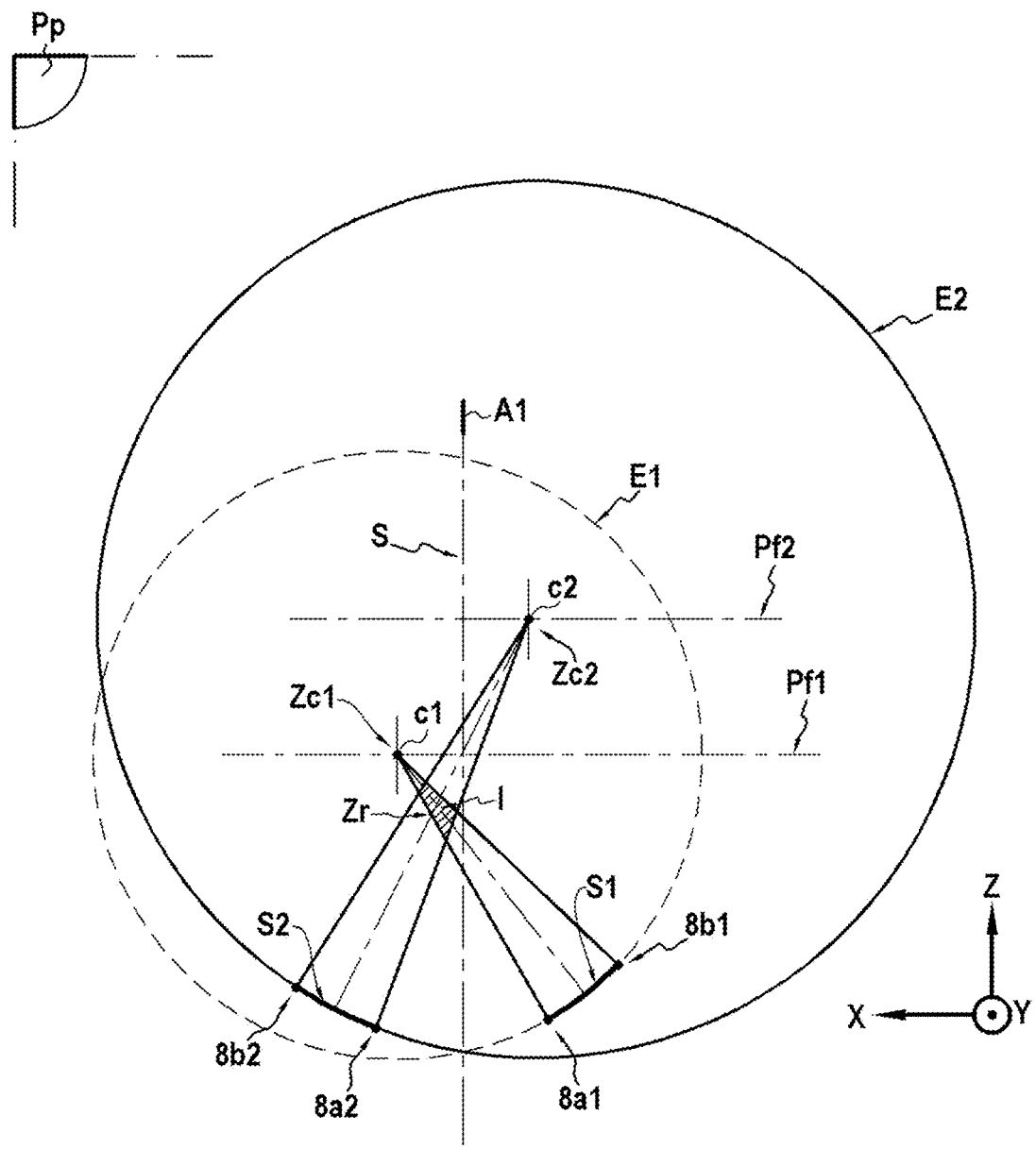

[Fig. 6A]
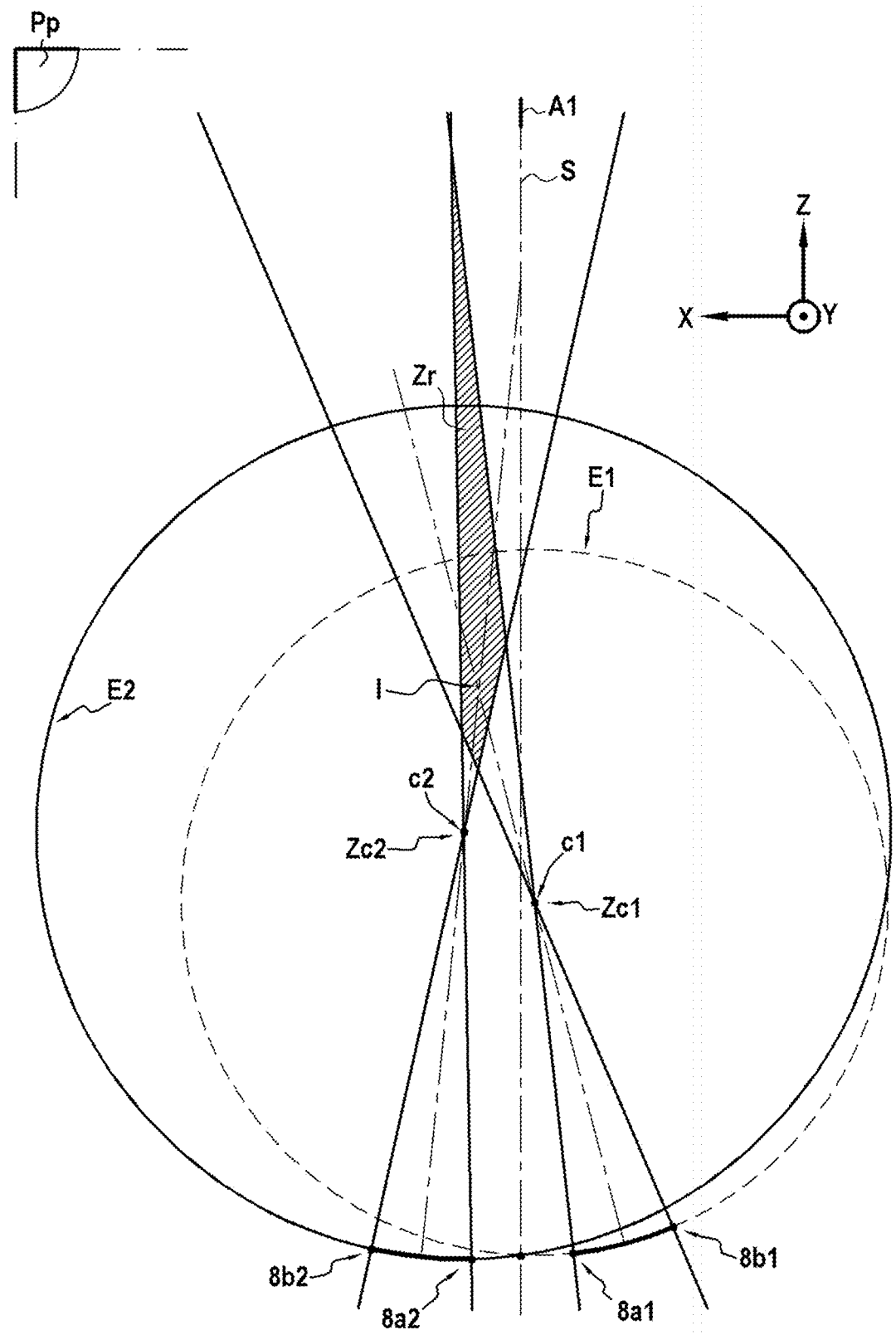

[Fig. 7A-7C]
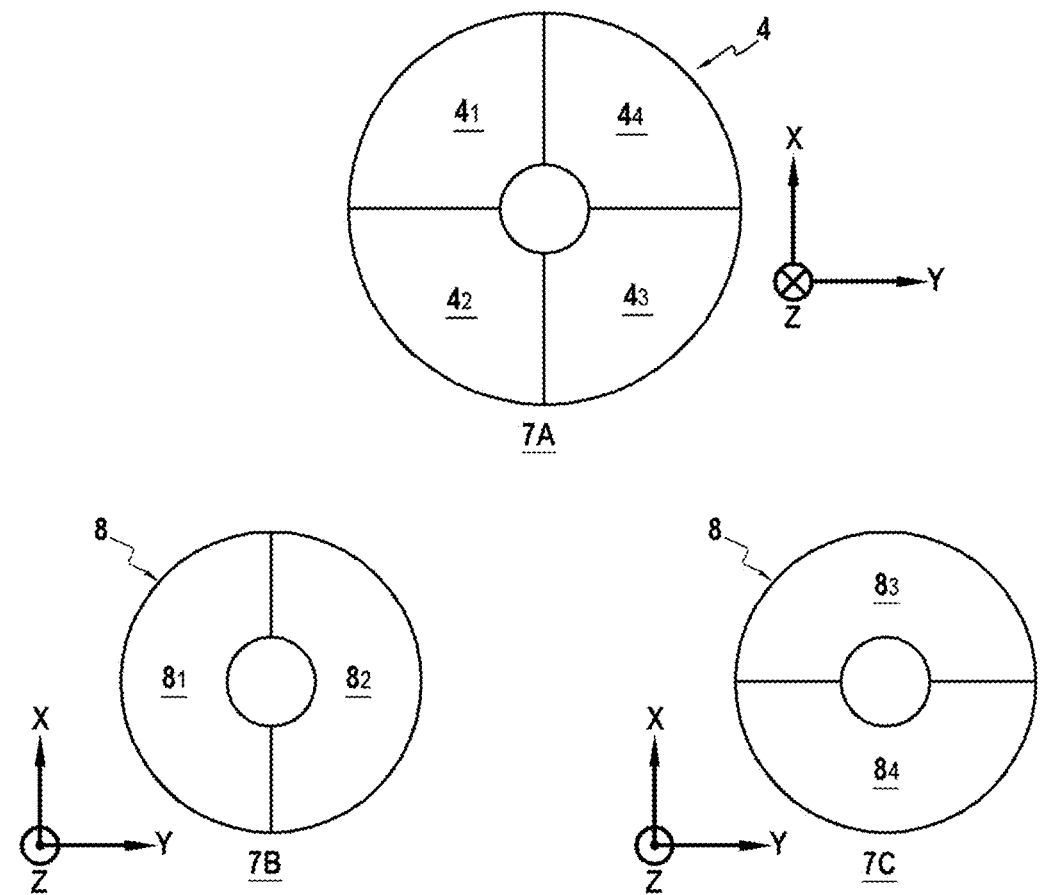
[Fig. 8A]
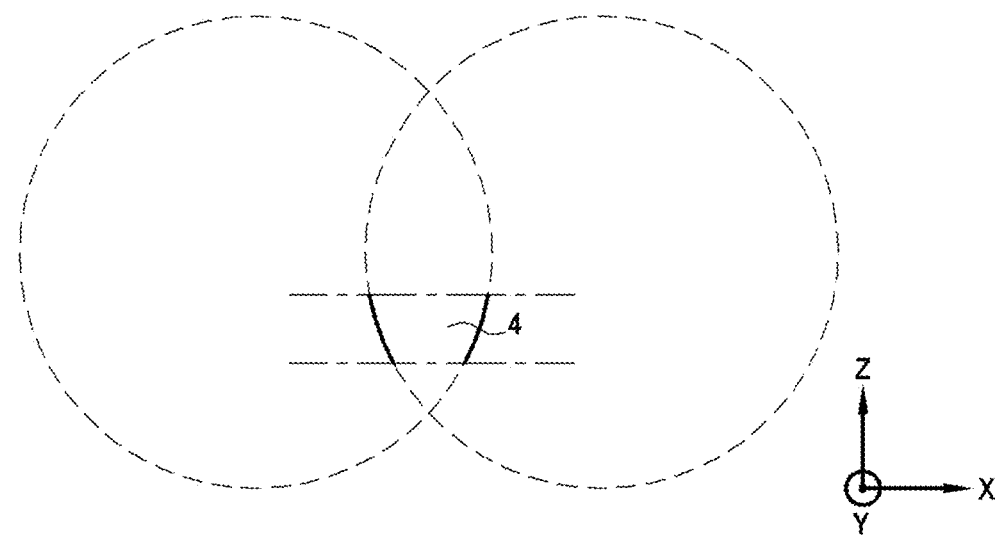

[Fig. 8B]
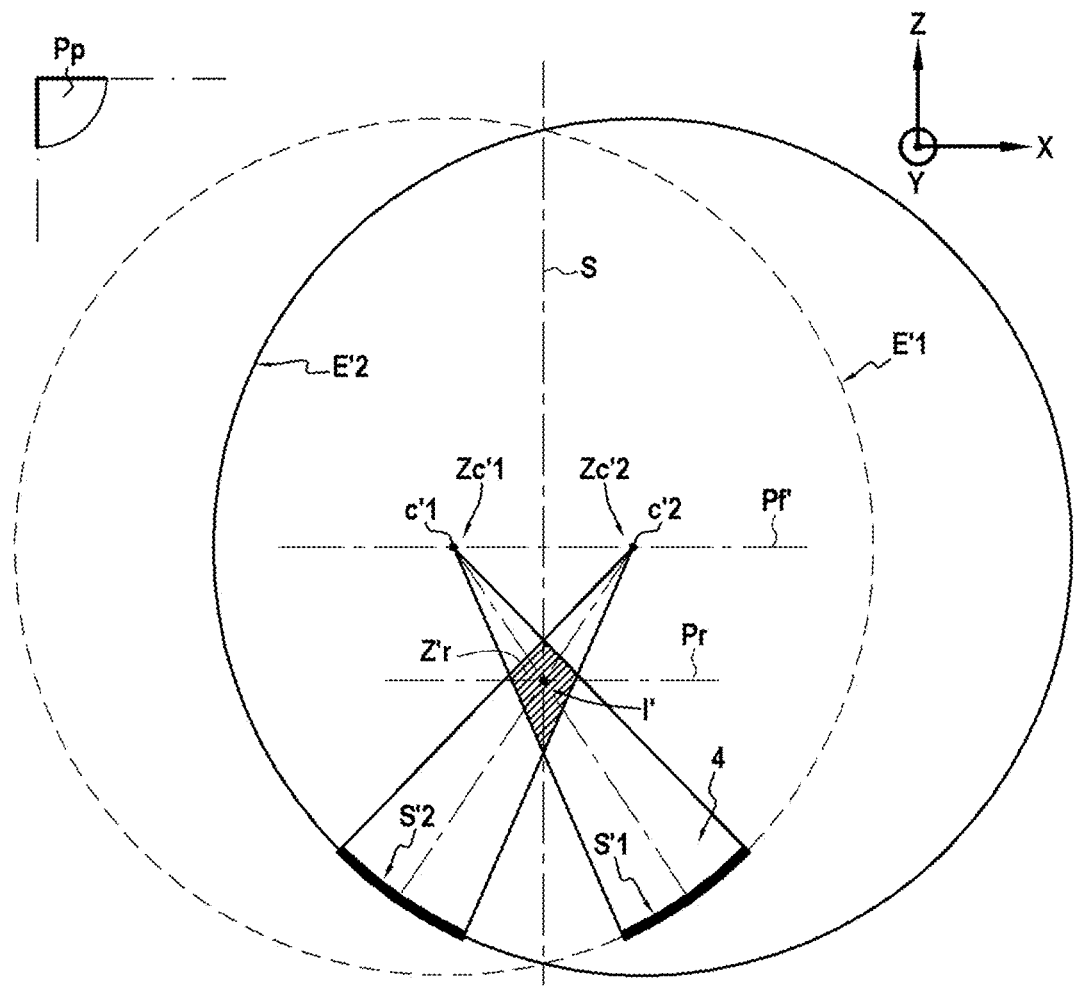
[Fig. 8C]
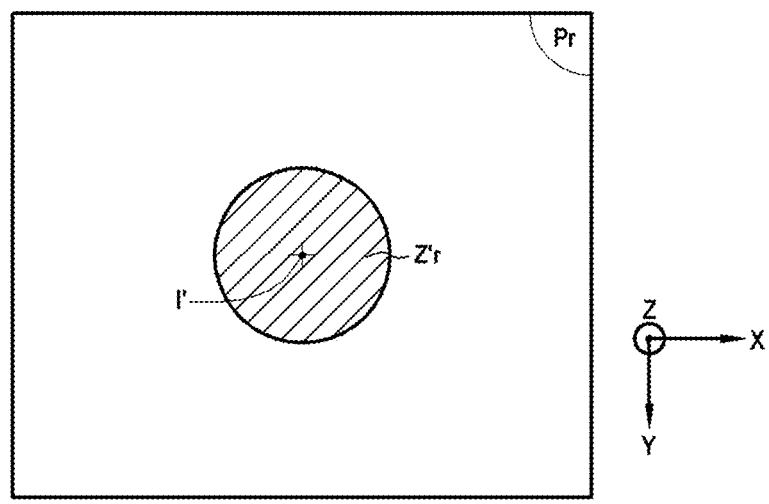

[Fig. 9A]
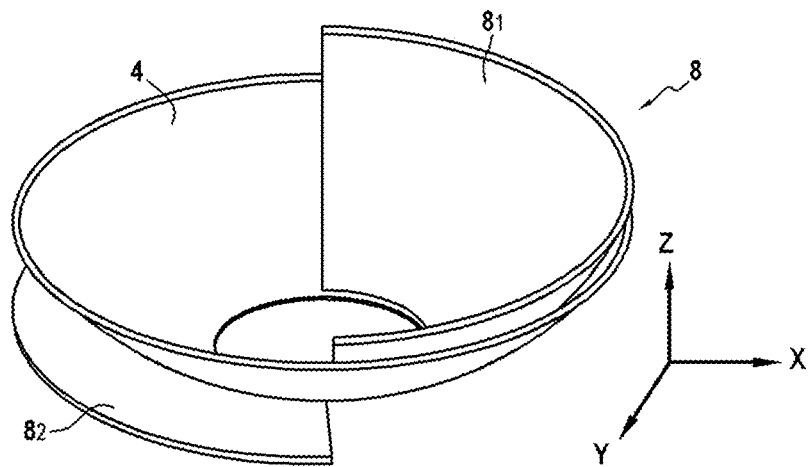
[Fig. 9B]
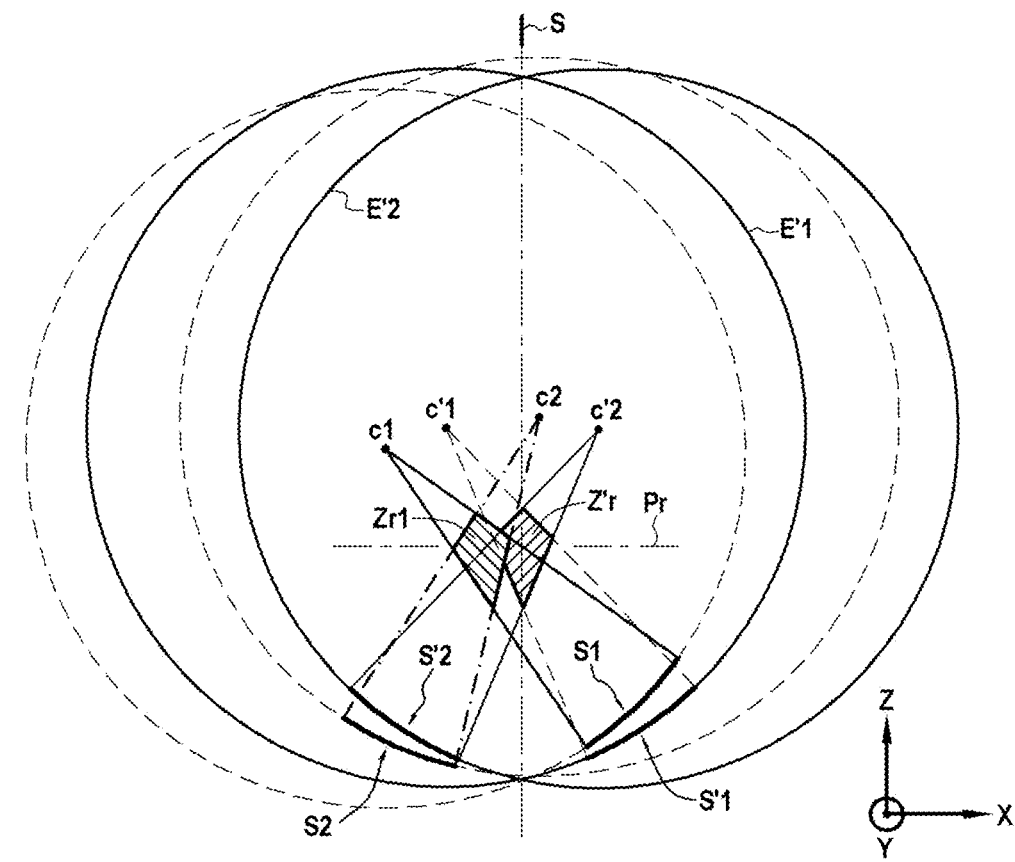

[Fig. 9C]
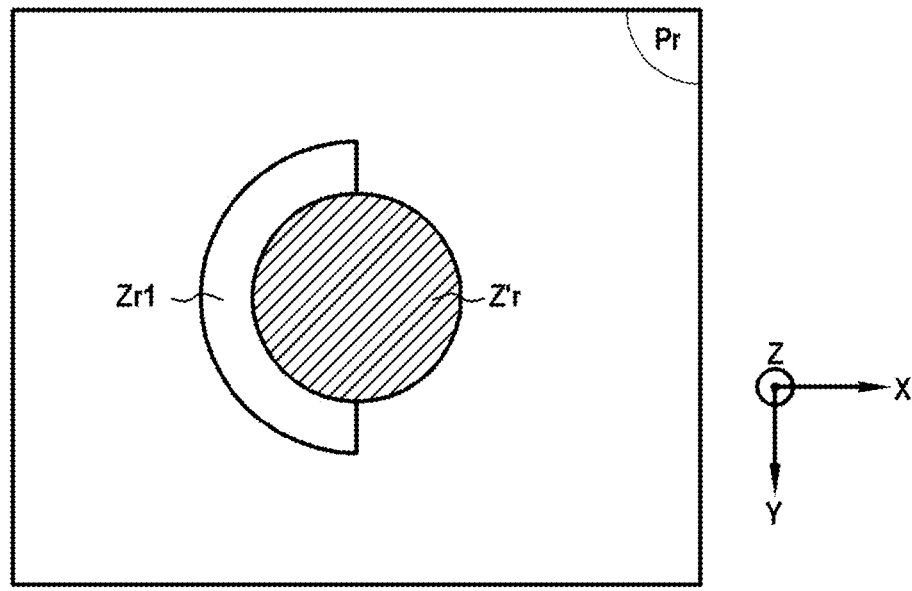
[Fig. 9D]
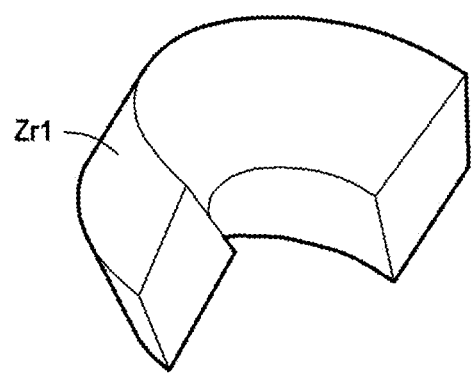

[Fig. 10A]
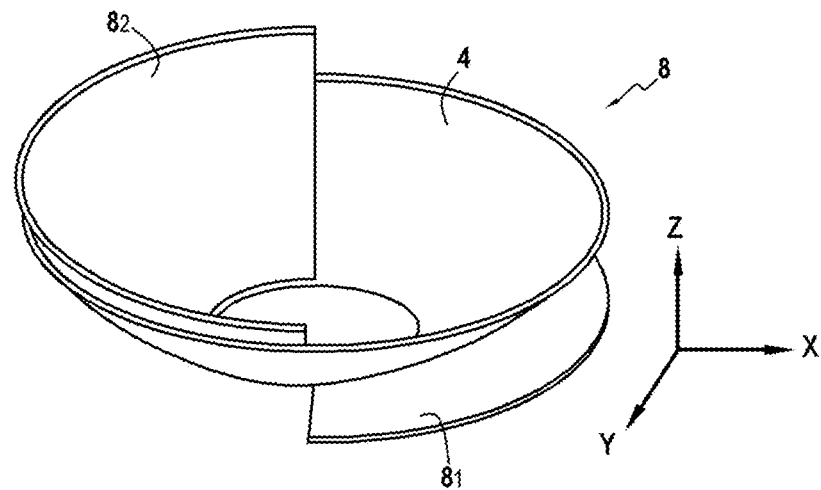
[Fig. 10B]
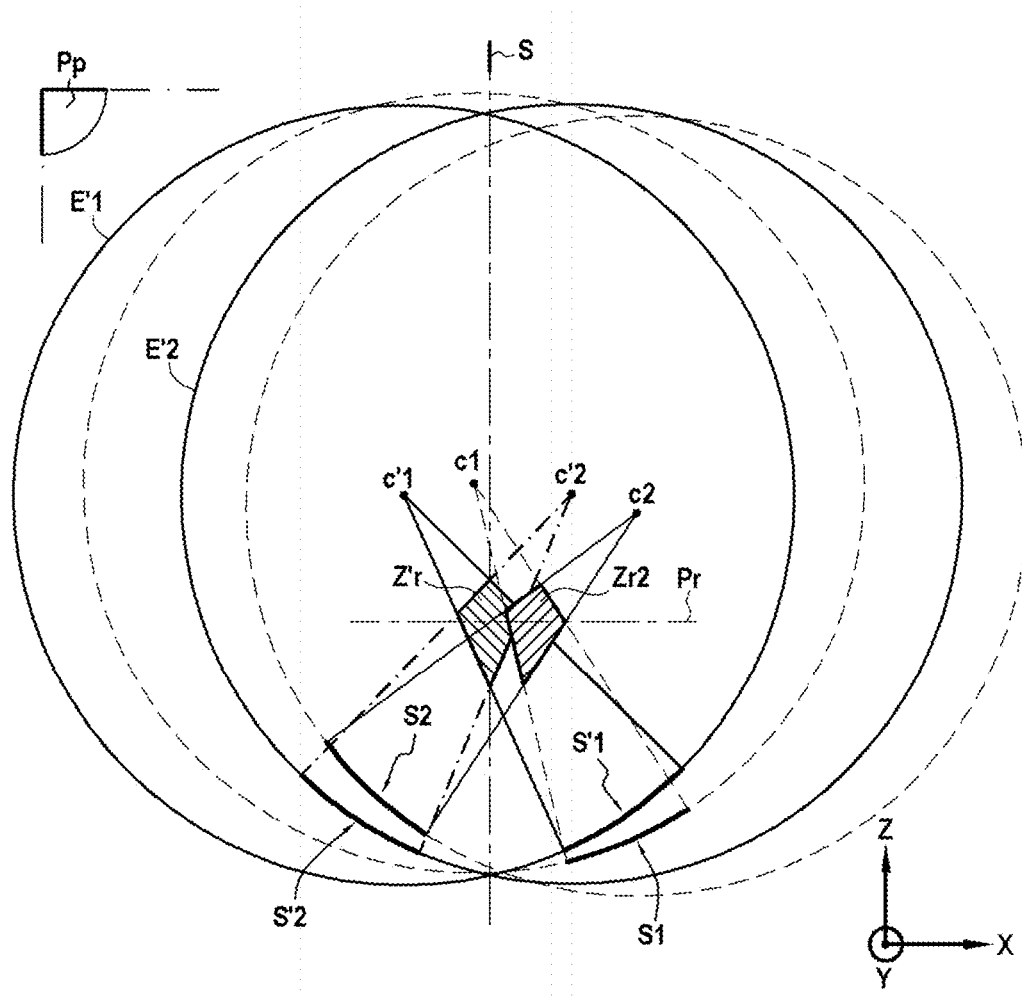

[Fig. 10C]
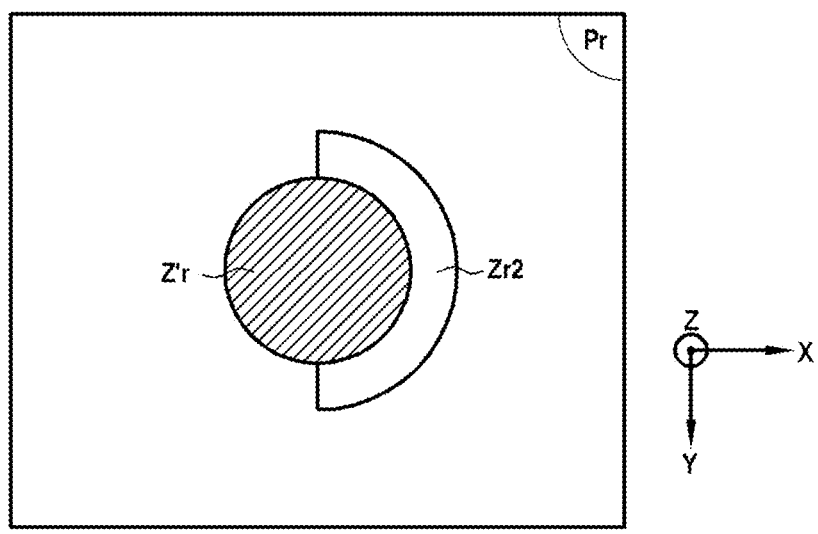
[Fig. 10D]
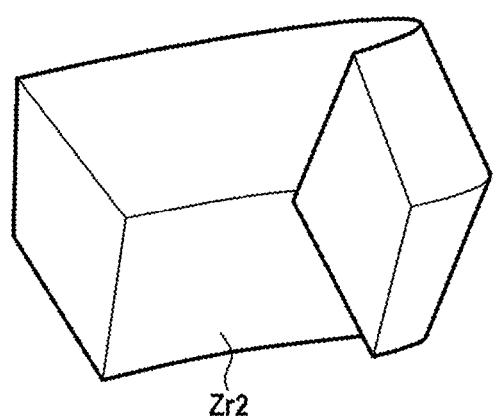

[Fig. 10E]
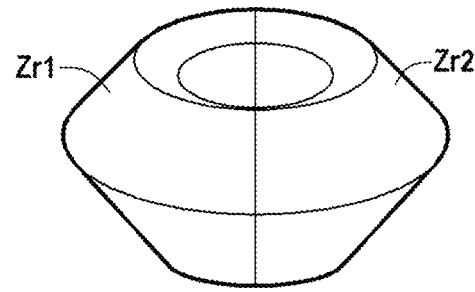
[Fig. 10F]
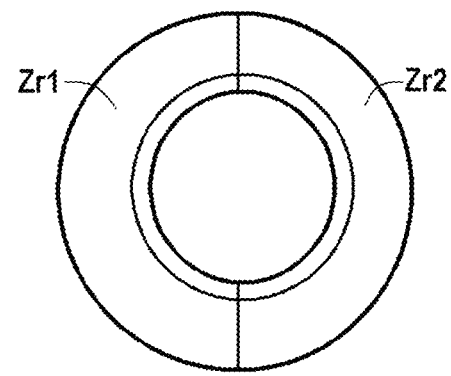
[Fig. 11A]
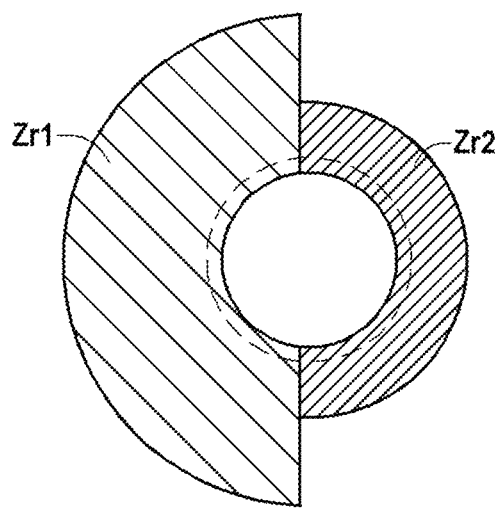

[Fig. 11B]
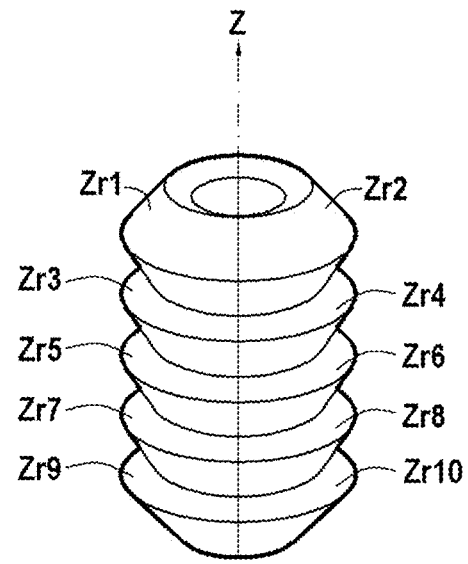
[Fig. 11C]
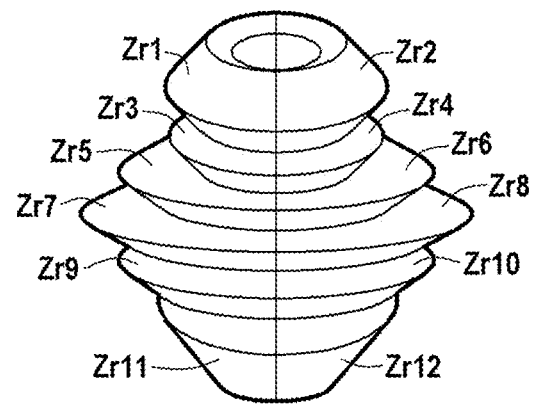

[Fig. 11D]
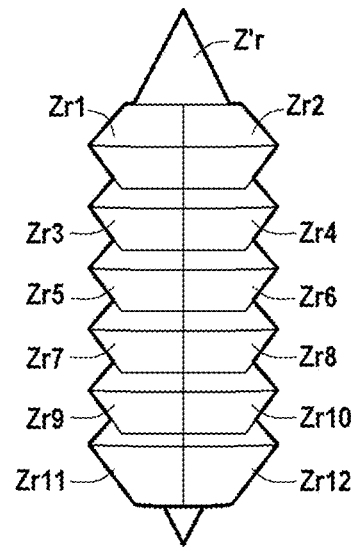
[Fig. 11E]
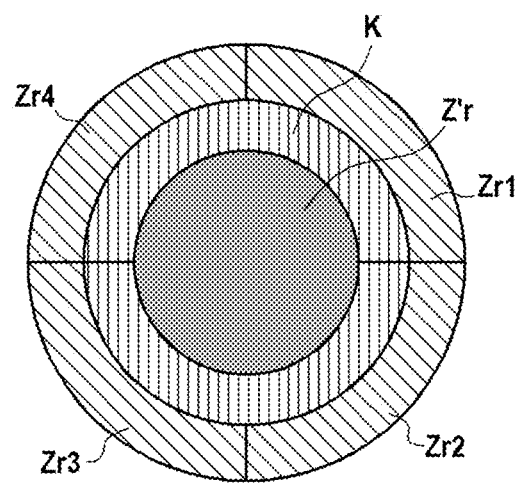

[Fig. 12]
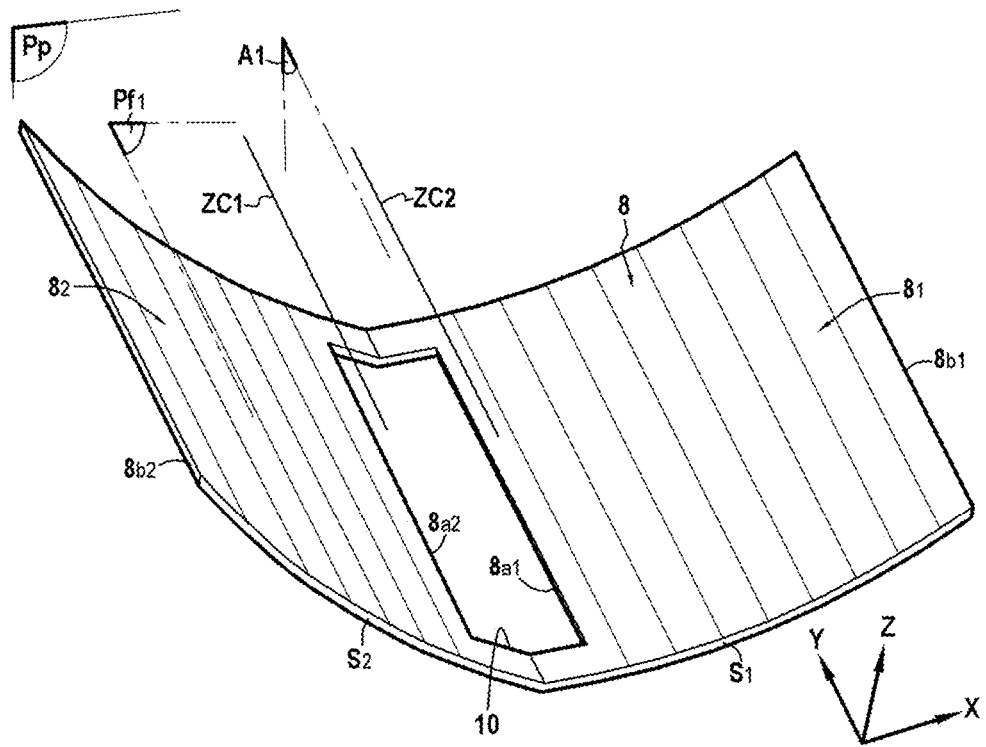
[Fig. 12A]
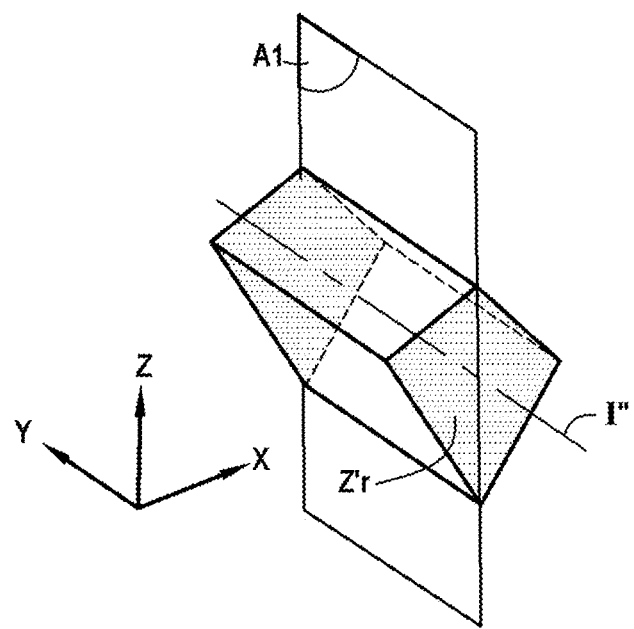

[Fig. 12B]
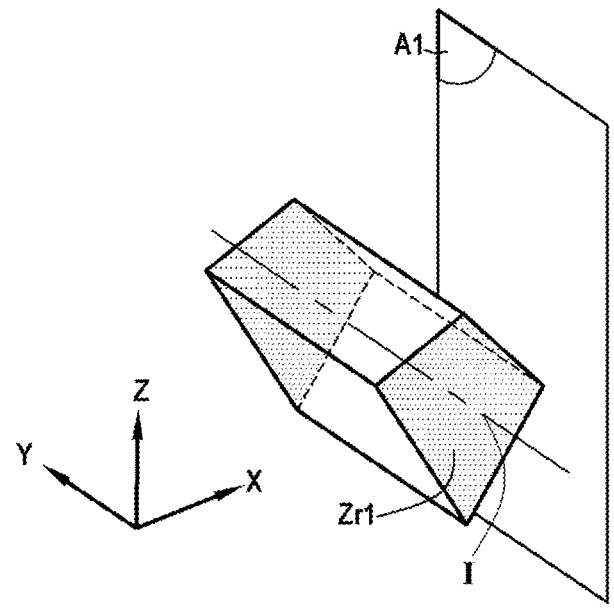
[Fig. 12C]
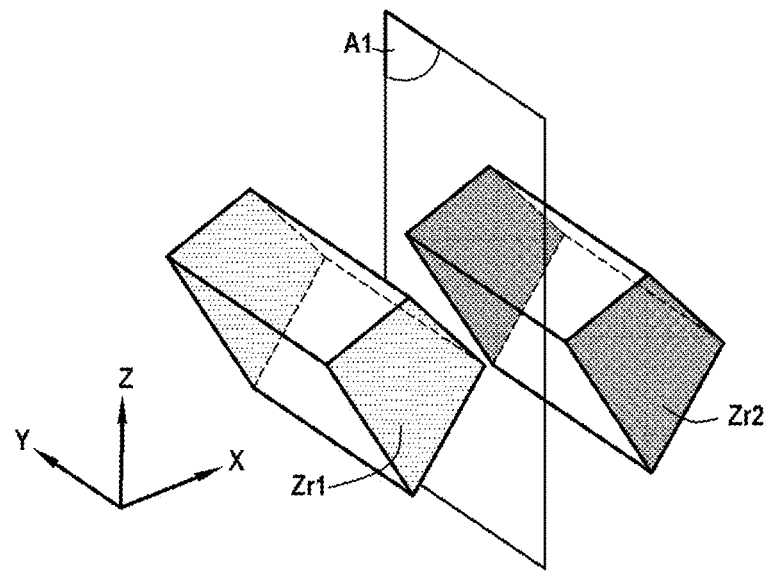

[Fig. 13A]
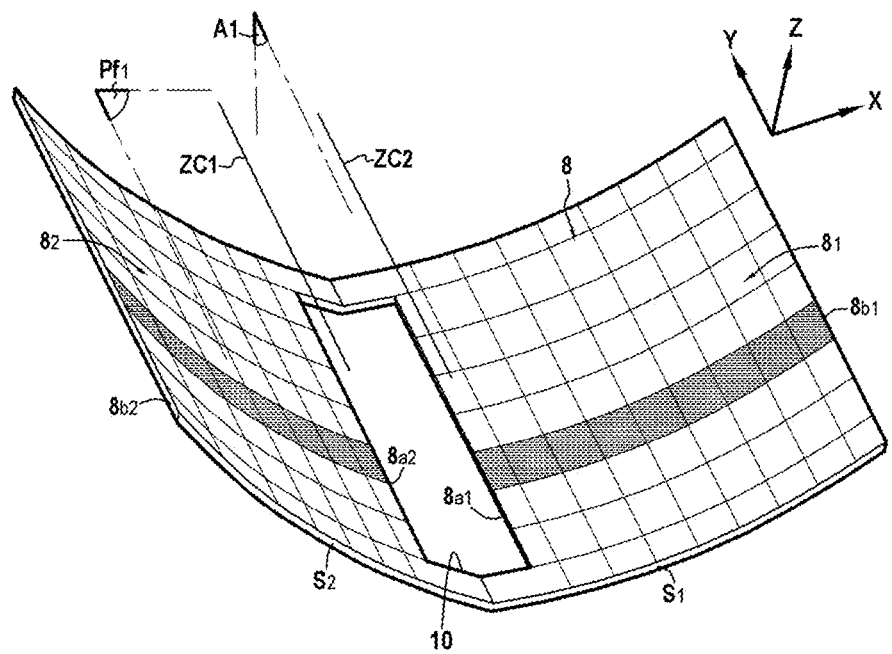
[Fig. 13B]
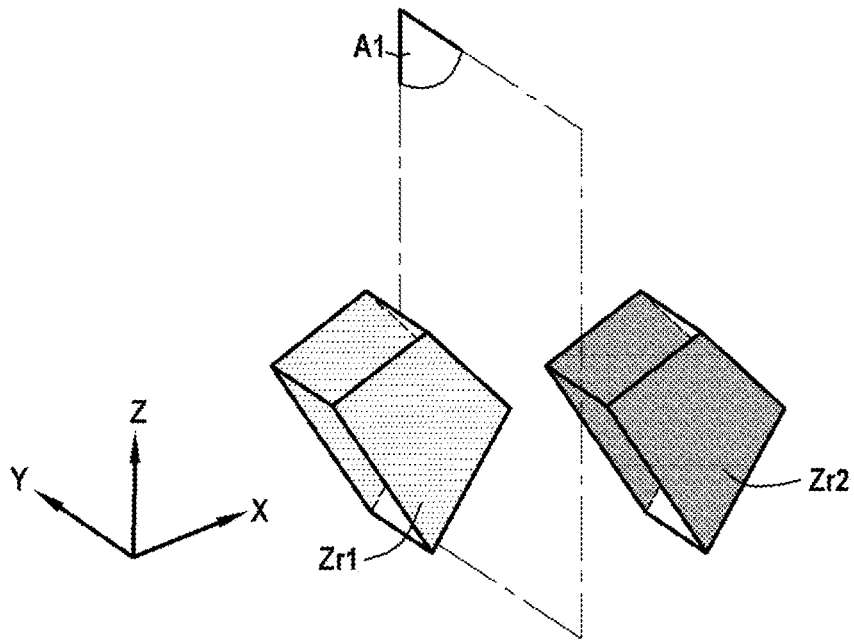

[Fig. 13C]
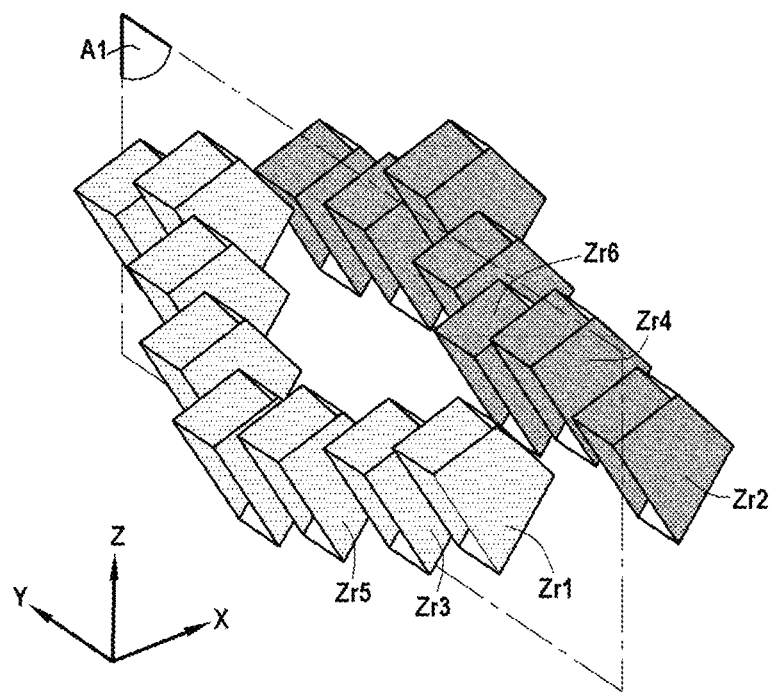
[Fig. 13D]
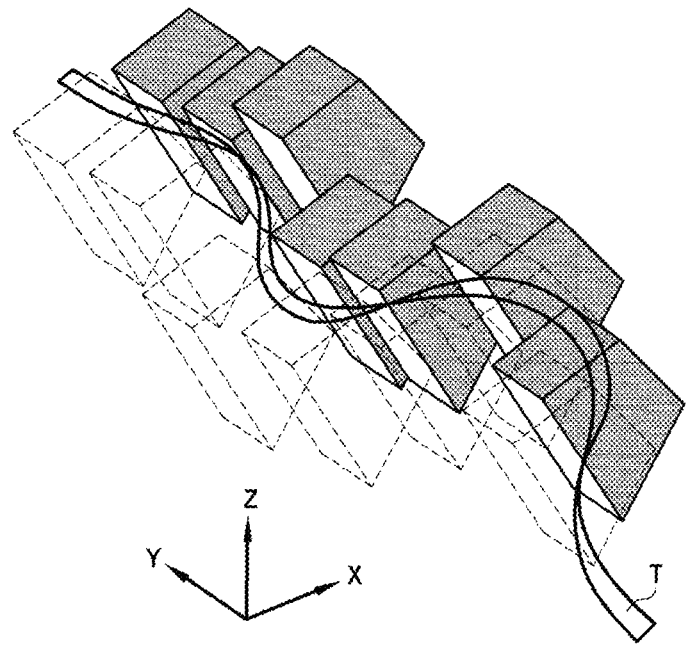

THERAPY APPARATUS FOR TREATING TISSUE BY THE EMISSION OF REMOTE CROSSED FOCUSED ULTRASOUND WAVES

CROSS-REFERENCE TO RELATED APPLICATIONS

This application claims priority to French patent application number 20 03282, filed Apr. 2, 2020, the contents of which are incorporated herein by reference.

TECHNICAL FIELD

The present invention relates to the technical field of apparatus or devices comprising an ultrasound probe formed by a plurality of ultrasound transducer elements, adapted to emit high-intensity focused ultrasound (HIFU).

The aim of the present invention applies particularly advantageously in the field of therapeutic treatments by focused ultrasound waves.

RELATED ART

It is known in particular from the publication "Kennedy, J. E., High-intensity focused ultrasound in the treatment of solid tumours. Nat Rev Cancer, 2005. 5(4): p. 321-7" that treatment by focused ultrasound waves creates biological lesions in tissue resulting from combining thermal effects and acoustic cavitation activity. Carrying out such treatment requires controlling the deposited energy and executing in minimum time of a lesion of a size appropriate to the tissue to be treated. Also, this treatment must be planned with the fewest possible shifts of the probe, since shifts introduce a sensitivity to movements and involve extension of treatment times, but also a lack of precision due to manual handling, or impose introduction of a robotic system to allow millimetric shifts. In addition, according to the tissue to be treated the shifts of the probe are not always practicable since acoustic windows available for treating tissue are sometimes highly restricted (Cf. "Aubry, J. F., et al., The road to clinical use of high-intensity focused ultrasound for liver cancer: technical and clinical consensus. J Ther Ultrasound, 2013. 1: p. 13").

The form of these tissular lesions originates directly from the form of the over-emission face of the ultrasound probe being used. For example, natural geometric focusing of a classic spherical ultrasound transducer HIFU is ellipsoidal due to diffraction. Also, the prior art has proposed various solutions for augmenting the size of the treated zone without having to shift the ultrasound probe.

Patent EP 0 214 782 describes a solution relating to an ultrasound transducer fitted with a lens for achieving annular focusing from a transducer of spherical geometry. This particular construction enlarges the focal zone to the size of the ring but also reveals a focal coverage zone situated on the central axis of the transducer originating from the intersecting of the ultrasound beams beyond the focusing plane of the transducer. This document provides a system for reducing the pressure field in this focal coverage zone to overcome the risk of secondary lesions.

Document WO2011/092683 describes a high-intensity-focused ultrasound probe comprising a first network of ultrasound transducers for focusing a first beam onto a target volume located in a lesion and a second network of ultrasound transducers for producing a second ultrasound beam focused on the same target volume such that interference between said first and second beams creates in said target volume an asymmetrical ultrasound field. This document describes various embodiments of the probe. The main drawback is that the two ultrasound beams are generated with different frequencies, which therefore requires more expensive electronics, more complex dephasing calculations and causes the appearance of secondary pressure lobes outside the target volume.

It should be noted that an ultrasound treatment probe can be used together with an imaging probe as proposed by patent EP0661029. In the same sense, U.S. Pat. No. 5,522,869 describes ultrasound energy treatment apparatus comprising a cylindrical probe with transducers in annular form.

Document XP 55009820 describes a therapy probe comprising a revolution emission face engendered by rotation about an axis of symmetry of a segment of concave curve with the centre of curvature located at a distance from the axis of symmetry. In a profile plane this emission face presents two segments of symmetrical concave curve relative to the axis of symmetry, with each segment of concave curve having an acoustic axis passing through the centre of curvature and the middle of the segment of concave curve. Such a transducer produces on the one hand a ring for focusing ultrasound waves delimited by the focal plane and on the other hand an intersection zone of ultrasound beams. As emerges clearly from this document, the intersection zone of ultrasound beams which correspond to the secondary pressure peak is situated behind the focal plane.

Patent EP 2 035 091 describes a HIFU transducer of toric form resulting in producing a focusing zone in the form of a ring at the centre of which the central focusing point is situated.

Patent EP 2 691 154 describes a therapy probe comprising an emission face of which the ultrasound emitters are adapted to create a first focal zone being defined in a focal plane and a second focal zone which is localised and situated between the first focal zone and the emission face, this second focal zone corresponding to a coverage zone of ultrasound beams.

Document "Vincenot, J., et al., Electronic beam steering used with a toroidal HIFU transducer substantially increases the coagulated volume. Ultrasound Med Biol, 2013. 39(7): p. 1241-54" describes the technique of electronic focusing for introducing a minimal area of freedom according to the axis perpendicular to the acoustic axis, consequently resulting in shifting of the lesion by a few millimetres according to this axis. This solution treats large-sized zones (50 cm$^3$) in minimal time (2 minutes).

Document WO2011/024074 proposes a solution for rectifying a large number of emitter elements and current generators employed in the electronic focusing technique which is conventionally expensive and complex. This solution aims to combine the emitter elements via packets so that a current generator can supply several of them in parallel, effectively reducing the number of current generators. Such combining can be modified electronically so as to allow shifting of the focal point adapted to the shape of the zones to be treated. If this solution does reduce the costs of control electronics, it does not reduce the cost of the transducer which comprises several hundreds of emitter elements. Producing this type of transducer requires the use of digital micromachining tools and needs multielement cutting difficult to carry out on a transducer made of conventional ceramic due to problems in electro-acoustic coupling between the elements.

Patent application WO2016144931 likewise discloses a system and a process for ultrasound wave emission for regenerating tissue implementing a determined scanning cycle.

Analysis of different solutions of the prior art leads to considering that there are difficulties to treatment of a tissue zone having complex configurations deviating from the acoustic axis. In fact, treatment by focused ultrasound waves in the broad sense of the term of a complex configuration requires a large number of elements (and therefore associated electronics) and lengthy treatment time. In the case of treatment by focused ultrasound waves by a toric transducer, the pressure remains maximal along the acoustic axis, implying difficulty in increasing zone treatment relative to the acoustic axis and in treating complex configurations which have no symmetry of revolution.

Such is the case especially of tissue to be treated in terms of breast cancer. The conical form of this organ having an areolar appearance at its apex associated with disparate sizes is most frequently left with one possible single position for the probe to treat the tumour. It is from this sole position that the entire target zone comprising the tumour must be treated, but also a certain number of healthy margins, involving the need to deposit energy in depth, but also deposit this energy in such a way that the final lesion is as much extended according to the axis perpendicular to the acoustic axis as in this axis itself.

Such is the case also for a target zone having a non-symmetrical volume along the acoustic axis and with a distance according to the axis perpendicular to the acoustic axis evolving along the acoustic axis. This target zone can for example adapt to a tumour of complex form or an organ of complex form (prostate, kidney, thyroid . . . ). Another configuration of target zones relates to a hollow volume extending around a non-rectilinear segment for example for treating tumours along arteries or veins, along the digestive tract, along bones, along the duct of Wirsung in the pancreas, the urethra or the biliary duct.

The aim of the present invention is to rectify the disadvantages of the various prior technical solutions by proposing novel low-cost therapy apparatus adapted to obtain a volume of biological lesions adapted to complex configurations of tissue to be treated while the acoustic treatment window is particularly restricted.

To achieve such an aim, the therapy apparatus for treating tissue by emission of focused ultrasound waves comprises a therapy probe having a transducer comprising a plurality of ultrasound emitters activated by signals delivered by a signal generator forming part of a control circuit, to define a creation surface of a pressure field of focused ultrasound waves.

According to the invention:
the creation surface is divided into at least N sectors (with N between 2 and 32) to focus the ultrasound waves on focal zones being defined in focal planes, the sectors of this creation surface having in a profile plane segments of concave curve of finite length, asymmetrical relative to a plane of symmetry or an axis of symmetry;
the centres of curvature are asymmetrical relative to the plane or to the axis of symmetry to the extent where the centres of curvature are situated at different distances from the plane of symmetry or from the axis of symmetry and/or at different depths taken according to the axis of symmetry;
each segment of concave curve has its own axis passing through a centre of curvature of said segment of concave curve and the middle of said segment of concave curve;
the individual axes intersect between the focal zones and the creation surface or beyond the focal zones such that the beams originating from the sectors intersect to create a focal coverage zone which is off-axis relative to the plane of symmetry or to the axis of symmetry and situated at a distance from the focal planes, between the focal zones and the creation surface or beyond the focal zones;
the sectors of this creation surface are engendered either by rotation of $2\pi/N$ of the segments of concave curve around the axis of symmetry or by translation of the segments of curve according to a direction perpendicular to the profile plane containing said segments of curve such that the sectors can create energy deposit zones with profiles corresponding to the focal coverage zones;
the segments of curve of the creation surface extend in the profile plane on either side of the axis of symmetry or of the plane of symmetry by being separate to allow positioning of the focal coverage zone at a distance from the creation surface.

According to a preferred realisation characteristic, the creation surface is divided into two sectors.

Advantageously, in the creation surface the internal edges delimit a housing for the mounting of an ultrasound imaging probe.

According to a first variant embodiment, the creation surface originates from a face defined by the transducer elements, of toric geometry engendered by the rotation of segments of concave curve around the axis of symmetry such that the segments of concave curve follow arcs of non-coinciding circles which intersect such that the focal zones have a form of portions of a circle.

According to a realisation characteristic, the face is truncated symmetrically relative to the axis of symmetry.

According to a second variant embodiment, the creation surface originates from a face defined by the transducer elements, of cylindrical geometry engendered by the translation according to a limited length, of two segments of curve according to a direction perpendicular to the profile plane containing said segments of curve such that the focal zones have a linear form.

According to an embodiment, the ultrasound emitters of the transducer define an emission face corresponding to the creation surface of a pressure field of focused ultrasound waves.

According to another embodiment, the signal generator forming part of the control circuit is controlled to deliver signals to activate the ultrasound emitters distributed in segments, with a law of delays or phases to realise the creation surface of a pressure field of focused ultrasound waves.

According to an advantageous variant embodiment, in an exposure phase the ultrasound emitters forming part of a sector and of the symmetrically opposite sector relative to the axis of symmetry are activated by signals delivered by the signal generator forming part of the control circuit to create the corresponding energy deposit zone.

According to a characteristic of the invention, in an exposure phase the ultrasound emitters forming part of a sector and of the symmetrically opposite sector relative to the axis of symmetry are activated by signals delivered by the signal generator forming part of the control circuit to create the corresponding energy deposit zone to one side of the plane of symmetry.

According to another characteristic of the invention, in a subsequent exposure phase the ultrasound emitters forming part of a sector and of the symmetrically opposite sector relative to the plane of symmetry are activated by signals delivered by the signal generator forming part of the control circuit to create the corresponding energy deposit zone to the side opposite the side in which the energy deposit zone of the preceding exposure phase is created.

Advantageously, the ultrasound emitters are distributed according to several sectors perpendicular to the plane of symmetry, and the ultrasound emitters of sectors in successive exposure phases are activated by signals delivered by the signal generator forming part of the control circuit to create energy deposit zones on either side of the plane of symmetry.

In terms of the invention, the ultrasound emitters in successive exposure phases for each of which the centres of curvature are situated at different distances from the plane of symmetry or the axis of symmetry and/or at different depths according to the vertical axis are activated by signals delivered by the signal generator forming part of the control circuit so as to obtain off-axis energy deposit zones.

According to an embodiment, the ultrasound emitters in successive exposure phases for which the centres of curvature are situated at different distances from the plane of symmetry or the axis of symmetry and/or at different depths according to the vertical axis are activated by signals delivered by the signal generator forming part of the control circuit so as to obtain for these successive exposure phases off-axis energy deposit zones of different positions with identical or different sizes.

According to another embodiment, in successive exposure phases the ultrasound emitters are activated by signals delivered by the signal generator forming part of the control circuit such that the distances and/or the depths of the centres of curvature are modified from one exposure phase to the other so that the energy deposit zones are concentric and/or symmetrical and/or asymmetrical and/or superposed according to the vertical axis.

According to an additional embodiment, in at least one complementary exposure phase the ultrasound emitters s are activated by signals delivered by the signal generator forming part of the control circuit o as to ensure the focusing of ultrasound waves in focal zones and to obtain a focal coverage zone centered relative to the plane of symmetry or to the axis of symmetry and situated at a distance from the focal planes between the focal zones and the emission face or beyond the focal zones.

The invention will be more clearly understood from the following detailed description with reference to the appended figures.

BRIEF DESCRIPTION OF THE DIAGRAMS

FIG. 1 is a schematic layout of therapy apparatus comprising a therapy probe illustrated according to a first variant embodiment, with a form of revolution about an axis of symmetry.

FIG. 2 is a schematic view showing an example of a creation surface of a pressure field of focused ultrasound waves realised according to the first variant embodiment, considered as a creation virtual surface.

FIG. 3 is a view explaining the principle for producing the creation surface of a pressure field of focused ultrasound waves, illustrated in FIG. 2.

FIG. 4 is an elevation section in the profile plane of a first example of the creation surface of a pressure field of focused ultrasound waves, which can be executed according to the first variant embodiment of the probe and according to a second variant embodiment, with a pseudo-cylindrical form.

FIG. 5 is an elevation section in the profile plane of a second example of the creation surface of a pressure field of focused ultrasound waves, which can be executed according to the first variant embodiment and according to the second variant embodiment of the probe.

FIG. 6 is an elevation section in the profile plane of a third example of the creation surface of a pressure field of focused ultrasound waves, which can be executed according to the first variant embodiment and according to the second variant embodiment of the probe.

FIG. 6A is an elevation section in the profile plane of a fourth example of the creation surface of a pressure field of focused ultrasound waves, which can be executed according to the first variant embodiment and according to the second variant embodiment of the probe.

FIG. 7A is a rear face view of a probe executed according to the first variant embodiment and illustrating the face of the probe being cut into four sectors. FIG. 7B is a view illustrating a creation surface of a pressure field of focused ultrasound waves, created by the probe illustrated in FIG. 7A. FIG. 7C is a view illustrating a creation surface of a pressure field of focused ultrasound waves, created by the probe illustrated in FIG. 7A.

FIG. 8A is a profile view of a probe executed according to the first variant embodiment in the form of a toric transducer with a central opening.

FIG. 8B is a sectional elevation view illustrating the principle of centered natural focusing executed by a probe realised according to the first variant embodiment in the form of a toric transducer illustrated in FIG. 8A.

FIG. 8C is a sectional elevation taken perpendicularly to the axis of symmetry according to a plane Pr and illustrating the form of the focal coverage zone of ultrasound beams at its centre, obtained according to the principle of centered natural focusing illustrated in FIG. 8B.

FIG. 9A is a schematic view showing an embodiment of a virtual surface for creating a pressure field of focused ultrasound waves, obtained by a transducer realised according to the first variant embodiment and such as illustrated in FIG. 8A.

FIG. 9B is a sectional elevation view in the profile plane, illustrating the principle of focusing by the transducer illustrated in FIG. 8A to produce a virtual surface for creating a pressure field of focused ultrasound waves, shown in FIG. 9A, so as to obtain an off-axis focal coverage zone of ultrasound beams illustrated relative to the focal coverage zone of ultrasound beams, obtained according to the principle of natural focusing.

FIG. 9C is a sectional elevation taken perpendicularly to the axis of symmetry according to a plane Pr and illustrating the form of the off-axis focal coverage zone of ultrasound beams, obtained according to the principle of the invention as well as the form of the focal coverage zone of ultrasound beams, obtained according to the principle of natural focusing.

FIG. 9D is a perspective view illustrating the form of the off-axis focal coverage zone of ultrasound beams, obtained according to the principle of the invention.

FIG. 10A is a schematic view showing another embodiment of a virtual surface for creating a pressure field of focused ultrasound waves, obtained by a transducer realised according to the first variant embodiment and such as illustrated in FIG. 8A.

FIG. 10B is a sectional elevation view in the profile plane illustrating the principle of focusing by the transducer illustrated in FIG. 8A to produce a virtual surface for creating a pressure field of focused ultrasound waves, shown in FIG. 10A, so as to obtain an off-axis focal coverage zone of ultrasound beams illustrated relative to the focal coverage zone of ultrasound beams, obtained according to the principle of natural focusing.

FIG. 10C is a sectional elevation taken perpendicularly to the axis of symmetry according to a plane Pr illustrating the form of the off-axis focal coverage zone of ultrasound beams, obtained according to the principle of the invention as well as the form of the focal coverage zone of ultrasound beams, obtained according to the principle of natural focusing.

FIG. 10D is a perspective view illustrating the form of the off-axis focal coverage zone of ultrasound beams, obtained according to the principle of focusing illustrated in FIG. 10B.

FIG. 10E is a perspective view illustrating the combined form of the off-axis focal coverage zones of ultrasound beams, obtained for two successive ultrasound exposure phases corresponding to the principles illustrated in FIGS. 9B and 10B.

FIG. 10F is a plan view illustrating the combined form of off-axis focal coverage zones of ultrasound beams, obtained for two successive ultrasound exposure phases corresponding to the principles illustrated in FIGS. 9B and 10B.

FIG. 11A is a plan view illustrating concentric and asymmetrical off-axis focal coverage zones during successive exposure phases.

FIG. 11B is a perspective view illustrating concentric, symmetrical and superposed off-axis focal coverage zones during successive exposure phases.

FIG. 11C is a perspective view illustrating concentric, symmetrical and superposed, off-axis focal coverage zones during successive exposure phases.

FIG. 11D is a perspective view illustrating centered natural focal coverage zones combined with concentric, symmetrical and superposed off-axis focal coverage zones during successive exposure phases.

FIG. 11E is a plan view illustrating a natural focal coverage zone enclosed by a focusing ring with two concentric off-axis focal coverage zones, itself enclosed by a focusing ring with four concentric off-axis focal coverage zones during successive exposure phases.

FIG. 12 is a perspective view illustrating an example of a transducer according to a second variant embodiment with a pseudo-cylindrical form for executing the invention.

FIG. 12A is a perspective view illustrating the form of the focal coverage zone of ultrasound beams obtained according to the principle of centered natural focusing realised by the transducer with a pseudo-cylindrical form illustrated in FIG. 12 during an exposure phase.

FIG. 12B is a perspective view illustrating a form of the off-axis focal coverage zone of ultrasound beams, obtained by the transducer with a pseudo-cylindrical form illustrated in FIG. 12 during an exposure phase.

FIG. 12C is a perspective view illustrating a symmetrical form of the off-axis focal coverage zone of ultrasound beams, obtained by the transducer with a pseudo-cylindrical form illustrated in FIG. 12 during a subsequent exposure phase.

FIG. 13A is a perspective view illustrating an example of execution of the second variant embodiment of the transducer with a pseudo-cylindrical form illustrated in FIG. 12.

FIG. 13B is a perspective view illustrating the symmetrical form of the off-axis focal coverage zone of ultrasound beams, obtained by the transducer illustrated in FIG. 13A during two successive exposure phases.

FIG. 13C is a perspective view illustrating the form of off-axis focal coverage zones of ultrasound beams, obtained by the transducer illustrated in FIG. 13A during successive exposure phases.

FIG. 13D is a perspective view illustrating the form of off-axis focal coverage zones of ultrasound beams, obtained by the transducer illustrated in FIG. 13A, in relation to a zone of ultrasound waves to be preserved during successive exposure phases.

DESCRIPTION OF EMBODIMENTS

As emerges in more detail from FIG. 1, the aim of the invention relates to therapy apparatus I in the general sense comprising a therapy probe 1 adapted to perform treatment of tissue of a living being by means of high-intensity focused ultrasound (HIFU). The therapy probe 1 comprises especially a transducer 2 comprising several ultrasound emitters 3 such as for example piezoelectric elements, defining an emission face 4 of focused ultrasound waves. These ultrasound emitters 3 are connected by means of coaxial cables 5 via an amplifier stage 6 to a control circuit 7 supplying signals to activate the ultrasound emitters 3. The control circuit 7 is not described in more detail as its realisation forms part of technical knowledge of the skilled person. This control circuit 7 conventionally comprises a controlled signal generator which is connected to the ultrasound emitters by means of the amplifier stage 6. In this way, each ultrasound emitter 3 is connected to its own signal generator.

The signal generator of the control circuit 7 activates the ultrasound emitters 3 distributed in segments and more precisely in segments of curves or straight lines to define a surface 8 for creating a pressure field of focused ultrasound waves. According to a first advantageous embodiment the signal generator forming part of the control circuit 7 is controlled to deliver signals to activate the ultrasound emitters 3 of the transducer 2, with a law of delays or phases to produce the creation surface 8 of a pressure field of focused ultrasound waves, this creation surface 8 being considered as a virtual creation surface distinct from the emission face 4 of the transducer (FIGS. 2, 9A, 10A). According to a second embodiment, the creation surface 8 of a pressure field of focused ultrasound waves corresponds to the face 4 of the transducer.

In other terms, the creation surface 8 of a pressure field of focused ultrasound waves corresponds either to the physical transducer or more precisely to the face 4 of the transducer 2 or to a virtual creation surface 8 by applying phases to the command channels of the transducer 2.

Even if activation of the ultrasound emitters 3 by a law of delays or phases is well known to the skilled person, the following description is a reminder of its principles.

P(r) the total pressure placed on each point of the zone of interest is defined by (Chavrier et coll. 2000):

$$P(\vec{r}) = \frac{j \cdot \rho \cdot c}{\lambda} \cdot \sum_{n=1}^{N} \int_{S} u_n \cdot e^{j \cdot \varphi_n} \cdot \frac{e^{-(f \cdot \alpha_{medium} + j \cdot k) \vec{r}}}{\vec{r}} \cdot dS$$

With P(r) the pressure (Pa) at point r, dS a set of elementary sources, ρ the volumic mass of the propagation medium, c the speed of ultrasound waves in the propagation medium, λ the wavelength, N the number of active elements of the transducer, S the surface of each source of emission, $u_n$ the normal speed of the element n, $\varphi_n$ the phase applied to the element n, $\alpha_{medium}$ the coefficient of attenuation of the medium, f the frequency of use of the transducer and finally k the wave number. According to the method known as "maximal response" (Curiel et coll. 2002), the phase originating from each element of the transducer at the preferred focusing point is obtained by fixing $\varphi_n=0$ in the line integral cited above.

Therefore the phase applied to each element to obtain a maximal signal at the preferred point is given by:

$$\text{Phase } [(n, M)] = \arctan \frac{\text{Im}[P(n, m)]}{\text{Re}[P(n, m)]}$$

With Im[P(n,m)] and Re[P(n,m)] respectively the imaginary and real parts of the pressure field at point M sent by the element n of the transducer. In this way, for each element, n, the delay $\tau_n$ is defined by:

$$\tau_n = \frac{\text{Phase}[P(n, M)]}{2\pi f}$$

Another calculation method consists of defining the path difference, for each element n, emitting between the natural focusing point and the preferred focusing point. The delay of each element is then defined by $$\tau_n = \frac{[d_{nat}] - [d_{foc}]}{c}$$

with $d_{nat}$ the distance between the element n and its natural focusing point, $d_{foc}$ the distance between the element n and the preferred focusing point and c the speed of ultrasound waves in the propagation medium. The phase is then obtained by $$\varphi = \frac{\tau_n * 360}{1/c}.$$

Another calculation method consists of defining a virtual ultrasound emitter, of different geometry but also cut into N elements, then having the centre of the first element of the real emitter coincide in the space with the centre of the first element of the virtual emitter. The distance $d_n$ between each respective element calculates the delay to be applied, defined by $$\tau_n = \frac{[d_n]}{c}$$

with c the speed of ultrasound waves in the propagation medium. The phase is then obtained by $$\varphi = \frac{\tau_n * 360}{1/c}.$$

As will be better understood within the description, the form of the creation surface 8 changes especially as a function of applications of the therapy apparatus. It therefore seems advantageous to arrange a probe with a face 4 of determined form easy to produce by the skilled person (FIG. 1 for example) and to generate creation surfaces 8 from this face 4, which have complex forms to make and are different to the form of the face 4 (as illustrated in FIG. 2 for example). But it can be possible to produce a transducer 2 with a face 4 the form of which corresponds to a creation surface 8 of a pressure field of focused ultrasound waves, such as that illustrated in FIG. 2, for example.

It should be noted that according to a first variant embodiment (FIGS. 1, 2, 3, 7A-7C, 8A-8C, 9A-9D, 10A-10F, 11A to 11E) the creation surface 8 has a form of revolution about an axis of symmetry S or, according to a second variant embodiment (FIGS. 12, 12A-12C, 13A-13D), a tubular pseudo-cylindrical form, or one composed of two portions of a cylinder having a plane of symmetry A1. It should be noted that FIGS. 4, 5, 6 and 6A are profile views for illustrating the creation surface 8 according to the first variant embodiment and according to the second variant embodiment. The axis of symmetry S which is defined according to the vertical direction Z corresponds to the axis of symmetry or to the acoustic axis of the face 4 of the transducer produced in the form of a revolution face. The plane of symmetry A1 is defined in the plane defined by the vertical direction Z and the transversal direction Y, this plane of symmetry being perpendicular to a profile plane Pp defined by the axes X, Z of a reference X, Y, Z. This plane of symmetry A1 is the plane of symmetry or the plane acoustic of the face 4 of the transducer.

In keeping with a characteristic of the invention illustrated more particularly in the figures, the creation surface 8 is divided into at least N sectors 8₁, 8₂, . . . , according to a radial cut at the acoustic axis S and containing the acoustic axis S or extending in mirror position relative to the plane acoustic A1. According to the first variant embodiment, the sectors are radial sectors relative to the acoustic axis S comprising for each of them ultrasound emitters 3 distributed in rings, while in the second variant embodiment the sectors are sectors in mirror position relative to the acoustic plane A1 comprising ultrasound emitters 3 distributed in linear segments. According to the first variant embodiment, the N radial sectors are advantageously between 2 and 8 and preferably equal to 2 (FIG. 2), while in the second variant embodiment the N sectors perpendicular to the acoustic plane A1 are between 2 and 32 (FIGS. 12 and 13A). Therefore, according to these advantageous variant embodiments the ultrasound emitters 3 of the transducer are limited in number, reducing the cost of such a transducer. For example, in the preferred two-sector variant each sector can comprise 32 ultrasound emitters 3. By way of simplification, only the term sector will be used throughout the rest of the description.

The creation surface 8 is divided into N sectors 8₁, 8₂, . . . , to focus the ultrasound waves on focal zones respectively $Zc_1$, $Zc_2$, . . . defining respectively in focal planes $Pf_1$, $Pf_2$, . . . . FIGS. 2 to 6, 9A, 10A, 12 illustrate a preferred embodiment in which the creation surface 8 is divided into two sectors $8_1$, $8_2$. FIG. 1 shows another embodiment for which the emission surface 4 is advantageously divided into two sectors $4_1$, $4_2$, for producing a creation surface 8 divided into two symmetrically opposite sectors.

FIG. 7A illustrates another embodiment for which the emission surface 4 is advantageously divided into four sectors $4_1$, $4_2$, $4_3$, $4_4$, for producing a creation surface 8 itself divisible into as many as four sectors $8_1$, $8_2$, $8_3$, $8_4$. Advantageously, the emission surface 4 is divided into four sectors to produce a creation surface 8 divided into two sectors according to two orthogonal planes (FIGS. 7B and 7C).

As emerges from more precisely from FIG. 4, in a profile plane Pp defined by the axes X, Z of a reference X, Y, Z, each sector $8_1$, $8_2$, . . . of this creation surface 8 presents a segment of concave curve S1, S2, . . . of finite length. As emerges from the figures, the segments of concave curve S1, S2 of sectors $8_1$, $8_2$ are delimited by end points respectively 8ai, 8b1 and 8a2, 8b2. In the profile plane Pp, the two segments of concave curve S1, S2, . . . are situated on either side of the plane of symmetry A or of the axis of symmetry S.

The segments of concave curves S1, S2, . . . are asymmetrical relative to an axis of symmetry S of the transducer 2 as in the first variant embodiment of the creation surface 8 with a form of revolution around the axis of symmetry (FIGS. 1, 2, 3, 7A-7C, 8A-8C, 9A-9D, 10A-10F, 11A to 11E) or relative to a plane of symmetry A1 of the transducer according to the second variant embodiment of the creation surface 8 with a pseudo-cylindrical form (FIGS. 12, 12A-12C, 13A-13D).

In keeping with FIGS. 4, 5, 6 and 6A which illustrate the creation surface 8 according to the first variant embodiment and according to the second variant embodiment, each segment of concave curve S1, S2, . . . has a centre of curvature respectively $c_1$, $c_2$, . . . corresponding to an ultrasound focusing zone Zc1, Zc2, . . . . In keeping with the invention, the segments of concave curve S1, S2, . . . of the sectors are asymmetrical relative to the plane of symmetry A1 or to the axis of symmetry S. Also, the centres of curvatures $c_1$, $c_2$, . . . are asymmetrical relative to the plane of symmetry A1 or to the axis of symmetry S to the extent where the centres of curvatures $c_1$, $c_2$, . . . are situated at different distances from the plane of symmetry A1 or the axis of symmetry S and/or at different depths taken according to the vertical direction Z.

According to the example illustrated in FIG. 4, comprising a first sector $8_1$ and a second sector $8_2$, the distance from the centre of curvature $c_1$ of the first sector $8_1$ relative to the axis of symmetry S or the plane of symmetry A1 is greater than the distance from the centre of curvature $c_2$ of the second sector $8_2$ relative to the axis of symmetry S or the plane of symmetry A1, these distances being taken according to the direction X perpendicular to the axis of symmetry S or to the plane of symmetry A1. It should be noted that in the example illustrated in FIG. 4, the centres of curvature $c_1$, $c_2$ are situated at the same depth according to the vertical direction Z (or axis of symmetry S), that is, they are situated according to the same straight line perpendicular to the axis of symmetry S or to the plane of symmetry A1. In other terms, the centres of curvatures $c_1$, $c_2$ are situated according to focal planes respectively $Pf_1$, $Pf_2$ which are joined.

FIG. 5 illustrates another embodiment for which the distance from the centre of curvature $c_1$ relative to the axis of symmetry S or the plane of symmetry A1 is different to the distance from the centre of curvature $c_2$ relative to the axis of symmetry S or the plane of symmetry A1, but also the depth according to the axis of symmetry S of the centre of curvature $c_1$ is different to the depth according to the axis of symmetry S of the centre of curvature $c_2$. Therefore, according to the example illustrated in FIG. 5, the focal plane $Pf_2$ containing the centre of curvature $c_2$ is, according to the axis of symmetry S, further away from the transducer than the focal plane $Pf_1$ containing the centre of curvature $c_1$. In other words, the centres of curvatures c1, c2 are situated according to focal planes respectively Pf1, Pf2 which are distinct.

Of course, the centres of curvatures $c_1$, $c_2$ are also considered as asymmetrical in the event where the depths according to the axis of symmetry S are different, whereas the distances from the centres of curvature $c_1$, $c_2$ relative to the axis of symmetry S or to the plane of symmetry A1 are identical. FIG. 6 illustrates this embodiment for which the distance from the centre of curvature $c_1$ relative to the axis of symmetry S or the plane of symmetry A1 is equal to the distance from the centre of curvature $c_2$ relative to the axis of symmetry S or of the plane of symmetry A1, whereas the depth according to the axis of symmetry S of the centre of curvature $c_1$ is different to the depth according to the axis of symmetry S of the centre of curvature $c_2$. According to this example, the centres of curvatures c1, c2 are situated according to focal planes respectively Pf1, Pf2 which are distinct.

Each segment of concave curve S1, S2, . . . of the sectors has its own axis respectively $a_1$, $a_2$, . . . passing through the centre of curvature $c_1$, $c_2$, . . . of said segment of concave curve and the middle of said segment of concave curve S1, S2, . . . .

According to another characteristic of the invention, the individual axes $a_1$, $a_2$, . . . of the segments of concave curve intersect to create a focal coverage zone Zr which is off-axis relative to the plane of symmetry A1 or relative to the axis of symmetry S. This focal coverage zone Zr corresponds to a focal coverage zone of ultrasound beams coming from the sectors $8_1$, $8_2$, . . . of the creation surface 8. In the embodiments illustrated in FIGS. 4 to 6 and 6A, in the profile plane Pp the focal coverage zone Zr presents a section with four sides in the form of a parallelogram delimited by the beams originating from the end points $8a_1$, $8b_1$ and $8a_2$, $8b_2$ of the segments of concave curve respectively S1, S2. This focal coverage zone Zr of ultrasound waves is advantageously used to create a voluminous biological lesion. Independently of the exploitation of the focal coverage zone Zr as treatment zone, the geometry of the lesions produced is controlled by the combination of the focal zones Zc1, Zc2, . . . and of the focal coverage zone Zr. In the present application the energy deposit zone corresponds to the focal coverage zone Zr, independently of the energy possibly deposited in the other focal zones.

This focal coverage zone Zr is off-axis in the sense where the individual axes $a_1$, $a_2$, . . . intersect at a common intersection point I which is situated outside the plane of symmetry A1 or outside the axis of symmetry S. The individual axes $a_1$, $a_2$, . . . intersect either at a depth situated between the focal zones $Zc_1$, $Zc_2$, . . . and the creation surface 8 as illustrated in FIGS. 3 to 6 and 12, or beyond the focal zones $Zc_1$, $Zc_2$, . . . as illustrated in FIG. 6A. The beams originating from the sectors $8_1$, $8_2$, . . . intersect such that the focal coverage zone Zr is situated according to the vertical direction Z, at a distance from the focal planes $Pf_1$, $Pf_2$, According to an advantageous embodiment characteristic the segments of curve S1, S2, . . . extend into the profile plane Pp, on either side of the axis of symmetry S or of the plane of symmetry A1, by being separate to allow positioning of the focal coverage zone Zr at a distance from the creation surface 8. Therefore, as is clearly evident from FIGS. 4 to 6 and 6A, the end points $8a_1$, $8a_2$, called internal, of the segments of curve are moved away relative to the axis of symmetry S or to the plane of symmetry A1.

The result of such an arrangement is that the creation surface 8, and subsequently the face 4, presents an opening 10 centered on the axis of symmetry S or on the plane of symmetry A1. The end points, called internal $8a_1$, $8a_2$, of the segments of curve situated in the profile plane Pp are set apart from each other by an internal distance Di taken according to the axis X between 10 mm and 120 mm. The choice of the gap between these end points causes modification to the position of the focal coverage zone Zr relative to the creation surface 8 (FIGS. 3, 4, 5, 8B, 9B, 10B) or modification to the form of the focal coverage zone Zr and its spread according to the axis Z (FIG. 6A) according to the relevant configuration. Advantageously, this opening 10 serves as housing for an ultrasound imaging probe.

It should be noted that in the profile plane Pp, the end points, called external $8b_1$, $8b_2$ of the sectors are separated by an external distance Ds for locating the focal coverage zone Zr at a distance from the focal planes. In other terms, the focal coverage zone Zr does not touch the focal plane $Pf_1$, $Pf_2$, . . . . In this way, the focal coverage zone Zr and the focal zones $Zc_1$, $Zc_2$, . . . are distinct or separated from each other.

According to another characteristic of the invention, the sectors $8_1$, $8_2$, . . . of the creation surface 8 are engendered, according to the first variant embodiment, either by rotation of 2 Π/N of the segments of concave curve S1, S2, . . . around the axis of symmetry S with N, the number of sectors, or, according to the second variant embodiment, by translation of the segments of curve S1, S2, . . . according to a direction Y perpendicular to the profile plane Pp containing said segments of curve S1, S2, . . . . The sectors $8_1$, $8_2$, . . . extend according to angular ranges or lengths of substantially identical values. In this way, in the event where the creation surface 8 is a surface of revolution divided into two sectors, each sector $8_1$, $8_2$ extends according to an angular range of 180° (FIG. 2).

The sectors $8_1$, $8_2$, . . . , situated in mirror position according to the axis of symmetry S or the plane of symmetry A1 create energy deposit zones with profiles corresponding to the focal coverage zones Zr and the focal zones Zc. According to the first variant embodiment for which the sectors of the creation surface 8 are engendered by the rotation of segments of concave curve around the axis of symmetry S, the focal zones $Zc_1$, $Zc_2$, . . . have forms in a portion of circles. In the case where the creation surface 8 is divided into two sectors $8_1$, $8_2$, the focal zones $Zc_1$ and $Zc_2$ are semi-circles extending according to an angular range of 180° (FIG. 3). According to the second variant embodiment for which the sectors $8_1$, $8_2$, . . . are engendered by translation of segments of concave curve according to the direction Y perpendicular to the profile plane Pp containing said segments of curve the focal zones $Zc_1$, $Zc_2$, . . . extend according to linear segments situated in the focal planes Pf1, Pf2, . . . , parallel to the direction Y (FIG. 12). In the case where the creation surface 8 is divided into two sectors $8_1$, $8_2$, the focal zones $Zc_1$ and $Zc_2$ extend according to two linear segments situated in the focal planes Pf1, Pf2, parallel to the direction Y (FIG. 12).

The creation surface 8 of a pressure field of focused ultrasound waves is obtained or realised by means of a transducer the face 4 of which is adapted to obtain the characteristics of the creation surface 8 described hereinabove.

According to the first variant embodiment for which the creation surface 8 is of revolution, the creation surface 8 originates from a face 4 defined by transducer elements, of advantageously toric geometry engendered by the rotation of segments of concave curve around the axis of symmetry S such that the segments of concave curve follow arcs of non-coinciding circles which intersect such that the focal zones $Zc_1$, $Zc_2$, . . . have a form of portions of a circle.

This face 4 of the transducer corresponds as illustrated in FIG. 8A to a cut-out of a portion of the envelope of a crossed torus, according to two planes perpendicular to the axis of symmetry S.

According to the second variant embodiment for which the creation surface 8 presents a pseudo-cylindrical or tubular form, the surface of the creation surface 8 originates from a face 4 defined by the transducer elements, of cylindrical geometry engendered by translation according to a limited length of two segments of curve according to a direction Y perpendicular to the profile plane Pp containing said segments of curve such that the focal zones Zc1, Zc2 . . . have a linear form.

FIG. 8A gives a preferred exemplary embodiment of the face 4 of the transducer 2 defined by segments of concave curve based on a crossed toric geometry.

As emerges from FIG. 8B, in the profile plane Pp the emission face 4 comprises two segments of concave curves $S'_1$, $S'_2$ which follow the arcs respectively of a first circle E'1 having a centre $c'_1$ and a second circle $E'_2$ having another centre $c'_2$ different to the centre $c'_1$ of the first circle E'1. The first and second circles E'1, E'2 do not coincide but intersect one another. One of the two segments of concave curve $S'_1$ (at the right in FIG. 8B), follows the arc of the first circle E'1, this arc of the first circle E'1 being situated inside the second circle E'2. Similarly, the other concave segment $S'_2$ (to the left in FIG. 8B) follows the arc of the second circle E'2, this arc of the second circle E'2 being situated inside the first circle E'1.

In the profile plane Pp this emission face 4 presents two segments of concave curve $S'_1$, $S'_2$ of finite length, symmetrical relative to the axis of symmetry S. Each concave segment $S'_1$, $S'_2$ of the emission face 4 therefore focuses the ultrasound waves on the centre $c'_1$, $c'_2$ of the circle in ultrasound focusing zones respectively Zc'1, Zc'2 situated beyond the axis of symmetry S relative to the corresponding emission face 4 $S'_1$, $S'_2$, these ultrasound focusing zones Zc'1, Zc'2 being defined in a focal plane Pf'.

The individual axes of the segments of concave curve $S'_1$, $S'_2$ cut the axis of symmetry S at a common point of intersection I' situated on this axis of symmetry S for the first variant embodiment. This common point of intersection of the individual axes is situated between the emission face 4 and the focal zones Zc'1, Zc'2 or beyond the focal plane Pf'. Therefore, the beams of the emission face 4 intersect to form the coverage zone Z'r of the ultrasound beams, which is symmetrical relative to the axis of symmetry S. This focal coverage zone Z'r of the ultrasound beams, called natural, is centered on the axis of symmetry S.

According to the first variant embodiment for which the transducer presents a form of revolution, the emission face 4 is obtained by rotation around the axis of symmetry S of a segment of concave curve illustrated by $S'_1$ and $S'_2$ in light of cutting of which the centre of curvature is situated to the side opposite said segment of curve relative to the axis of symmetry S. In the plane XY FIG. 8C illustrates the form of the focal coverage zone Z'r natural obtained by such a transducer of revolution. It should be remembered that in the case of a transducer of toric shape the transducer also deposits pressure in a focal plane in the form of a circle represented by the focal zones Zc'1, Zc'2 (FIG. 8B).

According to this first variant embodiment, the emission face 4 is a surface of revolution. This emission face 4 comprises for example a series of ultrasound transducer elements 3 mounted concentrically relative to each other and relative to the axis of symmetry S. Of course, as illustrated in FIG. 8A, it can be possible for the emission face 4 to be truncated symmetrically relative to the axis of symmetry S so that the transducer is limited to a portion of a crossed torus having a width of between 5 and 250 mm, for example. According to this embodiment, the transducer 2 comprises a series of ultrasound transducer elements 3 mounted concentrically relative to each other and relative to the axis of symmetry S such that they are distributed in the form of segments in the form of a ring.

According to the second variant embodiment for which the transducer 2 presents an emission face 4 comprising two portions of a cylinder, the emission face 4 is obtained according to the principle described hereinabove by producing concave curves $S'_1$, $S'_2$ of finite length, symmetrical relative to the plane of symmetry A1 and translation of these two segments of concave curve $S'_1$, $S'_2$ according to the direction Y perpendicular to the profile plane Pp containing said segments of concave curve. Therefore, each part of the emission face 4 focuses before, after or on the plane of symmetry A1, according to a linear segment extending into the focal plane, parallel to the direction Y. The individual axes of the segments of concave curve $S'_1$, $S'_2$ cut the plane of symmetry A1 into an axis of intersection I" included in the plane of symmetry A1 (FIG. 12A). As explained previously for the first variant embodiment, during a natural exposure phase the beams of the emission face 4 intersect to form the coverage zone Z'r of the ultrasound beams, which is symmetrical relative to the plane of symmetry A1. This focal coverage zone Z'r of the ultrasound beams, called natural, is centered on the plane of symmetry A1.

By means of the probe 1 provided with the emission face 4 described hereinabove, the creation surface 8 is created in keeping with the invention of which the characteristics have been described previously. In the following description the creation surface 8 is divided into two sectors $8_1$, $8_2$ by way of a preferred embodiment, but the aim of the invention can be executed for a creation surface 8 comprising a greater number of sectors. It should be noted that the transducer 2 corresponds to the physical or real transducer held in the hands of the user and that the creation surface 8 is formed by two virtual semi-transducers simulated by applying phases to each of the channels of the physical transducer after having subdivided the two sectors into several emitter elements. Determining these phases consists simply calculating, for each emitter element, the propagation time of ultrasound between the transducer 2 and the creation surface 8. According to the invention, virtually two parts of transducers are created for shifting the focusing elements without shifting the geometric elements specific to the physical transducer such as the acoustic axis or the axis of symmetry. In the following description an advantageous embodiment is described for which the signal generator forming part of the control circuit 7 is controlled to deliver signals to activate the ultrasound emitters 3 distributed in rings, with a law of delays or phases to produce the creation surface 8 of a pressure field of focused ultrasound waves.

By way of example, FIGS. 9A-9D and 10A-10F illustrate the operation of the ultrasound emitters 3 of the transducer illustrated in FIGS. 8A-8C to produce the creation surface 8 of the type of the first variant embodiment comprising two sectors $8_1$, $8_2$.

The signal generator forming part of the control circuit 7 is controlled to deliver signals in an exposure phase, to activate the ultrasound emitters 3 forming part of a sector $4_1$ and of the symmetrically opposite sector $4_2$ relative to the axis of symmetry S, to create the corresponding energy deposit zone.

In an exposure phase, the ultrasound emitters 3 of the two sectors $4_1$, $4_2$ are activated to obtain the creation surface 8 of the pressure field of focused ultrasound waves such that the latter form two emission faces, each obtained by rotation around the axis of symmetry S of different segments of concave curve $s_1$ and $s_2$. In this way the centres of curvature $c_1$, $c_2$ can be situated independently for each sector $8_1$, $8_2$ to the opposite side or not of said segment of curve relative to the axis of symmetry, accordingly creating an off-axis energy deposit zone Zr1 relative to the axis of revolution, as illustrated in FIGS. 9B and 9C. Activation of the ultrasound emitters 3 forming part of the sector $8_1$ and of the symmetrically opposite sector $8_2$ creates an energy deposit zone and especially an arched energy deposit zone $Zr_1$ with a profile corresponding to the focal coverage zone. This principle applies for the whole of the sectors comprising the transducer, effectively refining the form of the zone in which the pressure is deposited.

In a second exposure phase illustrated more precisely in FIGS. 10A-10D, the ultrasound emitters 3 of the two sectors $4_1$, $4_2$ are activated to create, relative to the arched energy deposit zone $Zr_1$ illustrated in FIG. 9D, an arched energy deposit zone $Zr_2$, symmetrical with a profile corresponding to the focal coverage zone. To perform this second exposure phase, the control circuit will again activate the entire surface of the transducer by inverting the phases applied between the sectors relative to the principle described previously.

It must be understood that the signal generator forming part of the control circuit 7 is controlled to deliver signals, in successive exposure phases, to activate the ultrasound emitters forming part of each of the sectors and of each symmetrically opposite sector relative to the axis of symmetry so as to create for each pair of sectors the corresponding energy deposit zone. In the example illustrated (FIGS. 10E-10F), it is possible to create a coagulation crown by two successive ultrasound exposures.

In the embodiment illustrated in FIGS. 10E-10F, the coagulation crown presents a constant profile or width. Of course, it is possible to have the profile or the width of the arched zones of energy deposit vary from one exposure phase to the other, as well as the height according to the direction Z, as for their positions relative to the axis of symmetry S.

Therefore, in general the signal generator forming part of the control circuit 7 is controlled to deliver signals to activate the ultrasound emitters in successive exposure phases for each of which the centres of curvature $c_1$, $c_2$, . . . are situated at different distances from the plane of symmetry A1 or the axis of symmetry S and/or at different depths according to the vertical axis Z so as to obtain off-axis energy deposit zones.

Therefore, the signal generator forming part of the control circuit 7 is controlled to deliver signals to activate the ultrasound emitters in successive exposure phases for which the centres of curvature $c_1$, $c_2$, . . . are situated at different distances from the plane of symmetry A1 or the axis of symmetry S and/or at different depths according to the vertical axis Z so as to obtain for these successive exposure phases off-axis energy deposit zones, of different positions with identical or different sizes.

In the example illustrated in FIGS. 10E-10F, the ultrasound emitters of the whole of the two sectors $8_1$, $8_2$ have undergone two activation phases for which the phases have been calculated so that the focal coverage zones Zr1 and Zr2 are symmetrical relative to the axis of symmetry S. This is reflected in the region of the creation surface 8 by transformation of the segment of concave curve $S_1$ into $S_2$ and of the segment of concave curve $S_2$ into $S_1$ during the second activation cycle.

FIG. 11A illustrates an embodiment in which for one exposure cycle the ultrasound emitters of the whole of the two sectors $8_1$, $8_2$ have undergone two activation phases for which the phases have been calculated so that the focal coverage zones Zr1 and Zr2 are asymmetrical relative to the axis of symmetry S. According to this example, the activation phases are performed with centres of curvature $c_1$, $c_2$, positioned in an adapted way to obtain asymmetrical focal coverage zones Zr1 and Zr2.

It seems possible to perform the exposure phases successively, such that from one exposure phase to the other, the centres of curvature are situated separately:
  or at different distances relative to the plane of symmetry A1 or the axis of symmetry S but at identical depths;
  or at the same distance according to the plane of symmetry A1 or the axis of symmetry S but at different depths;
  or at different distances relative to the plane of symmetry A1 or the axis of symmetry S and at different depths according to the plane of symmetry A1 or the axis of symmetry S.

It therefore seems possible, in successive exposure phases, to activate the ultrasound emitters such that the distances and/or the depths of the centres of curvature are modified from one exposure phase to the other so that the focal coverage zones are concentric and/or symmetrical and/or asymmetrical and/or superposed according to the vertical axis Z. The exposure phases can therefore be combined "infinitely" as a function of the more or less complex form of the volume to be treated.

FIG. 11B illustrates an embodiment for which the signal generator forming part of the control circuit 7 is controlled such that the ultrasound emitters of the whole of the two sectors $8_1$, $8_2$ undergo two activation phases for which the phases have been calculated so that the focal coverage zones Zr1 and Zr2 are symmetrical relative to the axis of symmetry S. These two activation phases form an exposure cycle which is repeated for different depths according to the vertical axis Z so as to obtain superposed crowns of energy deposit forming a cylinder having identical width and height from one exposure to the other.

FIG. 11C illustrates another embodiment for which the signal generator forming part of the control circuit 7 is controlled to deliver signals to activate the ultrasound emitters 3 such that the focal coverage zones Zr are situated at different distances and at different depths according to the vertical axis Z so as to obtain superposed focal coverage zones of variable widths and/or heights.

In the examples described hereinabove, the volume of energy deposit is hollow, that is, not in contact with the axis of symmetry S. Of course, the signal generator forming part of the control circuit can be controlled, in at least one complementary exposure phase, to deliver signals to activate the ultrasound emitters so as to ensure the focusing of ultrasound waves in focal zones and to obtain a focal coverage zone Z'r centered relative to the plane of symmetry A1 or to the axis of symmetry S and situated at a distance from the focal planes between the focal zones and the emission face or beyond the focal zones. Therefore, a complementary exposure phase, called natural according to the principle described in FIGS. 8A and 8B, can be performed for one or each exposure phase so as to complete the volume of energy deposit. Of course, this complementary exposure phase can be performed for one and/or the other of the embodiments described hereinabove. Therefore, FIG. 11D illustrates execution of a complementary exposure phase for the variant illustrated in FIG. 11B.

FIG. 11E illustrates in plan view a natural focal coverage zone Z'r centered relative to the axis of symmetry S enclosed by a focusing crown K made by two successive ultrasound exposures, as explained previously. It should be noted that this figure illustrates the making around the focusing crown K of an additional focusing crown produced by four successive ultrasound exposures embodied by a creation surface 8 divided into four sectors, to create four focal coverage zones Zr1 to Zr4.

By way of example the following description illustrates the executing of the creation surface 8 pertaining to the second variant embodiment. According to this example illustrated in FIG. 12, the first focal zone has a double linear form. The conditions for executing the invention described in relation to FIGS. 10A-10F, 11A-11E for the first variant embodiment apply in the same way for this creation surface 8 of pseudo-cylindrical form.

In keeping with the present invention, the ultrasound emitters 3 are cut out parallel to the plane of symmetry A1 and are activated with a law of delays or phases to produce the creation surface 8. The ultrasound emitters are distributed according to at least two sectors and according to the example illustrated in FIG. 12, with two sectors $8_1$, $8_2$ arranged symmetrically relative to the plane of symmetry A1.

Therefore, the signal generator forming part of the control circuit is controlled to deliver signals in an exposure phase to activate the ultrasound emitters forming part of a sector situated to one side of the plane of symmetry A1 and of the symmetrically opposite sector to create the corresponding energy deposit zone. It is therefore possible to produce a volume of energy deposit Zr1 (or a focal coverage zone Zr1) to one side of the plane of symmetry A1 and at a distance from this plane of symmetry (FIG. 12B). In the same way, it is possible to produce a volume of energy deposit Zr2 (or a focal coverage zone Zr2) to the other side of the plane of symmetry A1 and at a distance from this plane of symmetry A1 (FIG. 12C).

According to another advantageous embodiment the ultrasound emitters are distributed according to several sectors perpendicular to the plane of symmetry A1 and arranged opposite according to the plane of symmetry A1. In the example illustrated in FIG. 13A, nine sectors are situated on each side of the plane of symmetry A1, with each sector on one side being opposite a sector on the other side. Therefore, the signal generator forming part of the control circuit is controlled to deliver signals in an exposure phase, to activate the ultrasound emitters forming part of a sector and of the opposite sector, with a law of delays or phases to create the corresponding energy deposit zone to one side of the plane of symmetry (FIG. 13A). The ultrasound emitters of the opposite sectors are capable of creating volumes of energy deposit on either side of the plane of symmetry A1. FIG. 13B illustrates the realisation of two volumes of energy deposit situated on either side of the plane of symmetry A1. The thickness of the volume of energy deposit corresponds to the width of a sector of the transducer.

As explained previously, each volume of energy deposit can vary in form, size and location especially by playing on the position of the centres of curvature. Successive activation of the different sectors of the transducer produces a hollow volume of energy deposit of variable thickness (FIG. 13C).

This solution applies particularly advantageously for treating target zones extending along a non-rectilinear segment T, for example to enable treatment of tumours along arteries or veins, along the digestive tract, along bones, along the duct of Wirsung in the pancreas, the urethra or the biliary duct (FIG. 13D).

It emerges from the preceding description that the aim of the invention produces a shift of the focal zone in depth (according to the acoustic axis and a shift in a plane parallel to the transducer (perpendicular to the acoustic axis), effectively reducing the number of emitters. Contrary to the prior art which proposes creating a focal point and shifting in space (electronic focusing), the aim of the invention is to directly create a volume (portion of crown) obtained by calculating a "virtual" creation surface or "virtual" transducer and shifting this volume without involving a large number of emitters. This invention therefore reduces control electronics costs but also the cost of the transducer.

The invention claimed is:

1. A therapy apparatus for treating tissue by the emission of focused ultrasound waves, comprising:
   a therapy probe having a transducer comprising a plurality of ultrasound emitters defining an emission face of focused ultrasound waves having an axis of symmetry corresponding to the acoustic axis, or a plane of symmetry corresponding to the acoustic plane, these ultrasound emitters being activated by signals delivered by a signal generator forming part of a control circuit, to define a creation surface of a pressure field of focused ultrasound waves;
   wherein the creation surface is divided into N sectors, where N is from 2 to 32, to focus the ultrasound waves on focal zones being defined in focal planes, the sectors of this creation surface having in a profile plane segments of concave curve of finite length, asymmetrical relative to the plane of symmetry, or the axis of symmetry;
   wherein the centres of curvature are asymmetrical relative to the plane, or to the axis of symmetry, to the extent where the centres of curvature are situated at different distances from the plane of symmetry, or from at least one of the axis of symmetry, and at different depths taken according to the axis of symmetry;
   wherein each segment of concave curve has its own axis passing through a centre of curvature of said segment of concave curve and the middle of said segment of concave curve;
   wherein the individual axes intersect between the focal zones and the creation surface, or beyond the focal zones, such that the beams originating from the sectors intersect to create a focal coverage zone which is off-axis relative to the plane of symmetry, or to the axis of symmetry, and situated at a distance from the focal planes, between the focal zones and the creation surface, or beyond the focal zones;
   wherein the sectors of this creation surface are engendered either by rotation of 2π/N of the segments of concave curve around the axis of symmetry, or by translation of the segments of curve according to a direction perpendicular to the profile plane containing said segments of curve such that the sectors can create energy deposit zones with profiles corresponding to the focal coverage zones;
   wherein the segments of curve of the creation surface extend in the profile plane on either side of the axis of symmetry, or of the plane of symmetry, by being separate to allow positioning of the focal coverage zone at a distance from the creation surface;
   wherein each one of the plurality of ultrasound emitters is connected to its own signal generator;
   wherein, in an exposure phase, the ultrasound emitters forming part of a sector, and of the symmetrically opposite sector relative to the plane of symmetry, are activated by signals delivered by the signal generator forming part of the control circuit to create the corresponding energy deposit zone to one side of the plane of symmetry; and
   wherein, in a subsequent exposure phase, the ultrasound emitters forming part of a sector, and of the symmetrically opposite sector relative to the plane of symmetry, are activated by signals delivered by the signal generator forming part of the control circuit to create the corresponding energy deposit zone of the side opposite the side in which the energy deposit zone of the preceding exposure phase is created.

2. The therapy apparatus according to claim 1, wherein the creation surface is divided into two sectors.

3. The therapy apparatus according to claim 1, wherein, in the creation surface, the internal edges delimit a housing for the mounting of an ultrasound imaging probe.

4. The therapy apparatus according to claim 1, wherein the creation surface originates from a face defined by the transducer elements of toric geometry engendered by the rotation of segments of concave curve around the axis of symmetry such that the segments of concave curve follow arcs of non-coinciding circles which intersect such that the focal zones have a form of portions of a circle.

5. The therapy apparatus according to claim 4, wherein the face is truncated symmetrically relative to the axis of symmetry.

6. The therapy apparatus according to claim 1, wherein the creation surface originates from a face defined by the transducer elements of cylindrical geometry engendered by translation according to a limited length of two segments of curve according to a direction perpendicular to the profile plane containing said segments of curve such that the focal zones have a linear form.

7. The therapy apparatus according to claim 1, wherein the ultrasound emitters of the transducer define an emission face corresponding to the creation surface of a pressure field of focused ultrasound waves.

8. The therapy apparatus according to claim 1, wherein the signal generator forming part of the control circuit is controlled to deliver signals to activate the ultrasound emitters distributed in segments, with a law of delays or phases to create the creation surface of a pressure field of focused ultrasound waves.

9. The therapy apparatus according to claim 1, wherein, in an exposure phase, the ultrasound emitters forming part of a sector and of the symmetrically opposite sector relative to the axis of symmetry are activated by signals delivered by the signal generator forming part of the control circuit to create the corresponding energy deposit zone.

10. The therapy apparatus according to claim 1, wherein the ultrasound emitters are distributed according to several sectors perpendicular to the plane of symmetry; and wherein the ultrasound emitters of sectors in successive exposure phases are activated by signals delivered by the signal generator forming part of the control circuit to create energy deposit zones on either side of the plane of symmetry.

11. The therapy apparatus according to claim 1, wherein the ultrasound emitters in successive exposure phases for each of which the centres of curvature are situated at different distances from the plane of symmetry, or of at least one of the axis of symmetry and at different depths according to the vertical axis, are activated by signals delivered by the signal generator forming part of the control circuit so as to obtain off-axis energy deposit zones.

12. The therapy apparatus according to claim 11, wherein the ultrasound emitters in successive exposure phases for which the centres of curvature are situated at different distances from the plane of symmetry, or from at least one of the axis of symmetry and at different depths according to the vertical axis, are activated by signals delivered by the signal generator forming part of the control circuit so as to obtain, for these successive exposure phases, off-axis energy deposit zones of different positions with identical or different sizes.

13. The therapy apparatus according to claim 9, wherein, in successive exposure phases, the ultrasound emitters are configured so that at least one of the distances and the depths of the centres of curvature are modified from one exposure phase to the other are activated by signals delivered by the signal generator forming part of the control circuit, wherein the energy deposit zones are at least one of concentric, symmetrical, asymmetrical, and superposed according to the vertical axis.

14. The therapy apparatus according to claim 1, wherein, in at least one complementary exposure phase, the ultrasound emitters are activated by signals delivered by the signal generator forming part of the control circuit so as to ensure the focusing of ultrasound waves in focal zones and to obtain a focal coverage zone centred relative to the plane of symmetry, or to the axis of symmetry, and situated at a distance from the focal planes between the focal zones and the emission face, or beyond the focal zones.

15. A therapy apparatus for treating tissue by the emission of focused ultrasound waves, comprising:

a therapy probe having a transducer comprising a plurality of ultrasound emitters defining an emission face of focused ultrasound waves having an axis of symmetry corresponding to the acoustic axis, or a plane of symmetry corresponding to the acoustic plane, these ultrasound emitters being activated by signals delivered by a signal generator forming part of a control circuit, to define a creation surface of a pressure field of focused ultrasound waves;

wherein the creation surface is divided into N sectors, where N is from 2 to 32, to focus the ultrasound waves on focal zones being defined in focal planes, the sectors of this creation surface having in a profile plane segments of concave curve of finite length, asymmetrical relative to the plane of symmetry, or the axis of symmetry;

wherein the centres of curvature are asymmetrical relative to the plane, or to the axis of symmetry, to the extent where the centres of curvature are situated at different distances from the plane of symmetry, or from at least one of the axis of symmetry, and at different depths taken according to the axis of symmetry;

wherein each segment of concave curve has its own axis passing through a centre of curvature of said segment of concave curve and the middle of said segment of concave curve;

wherein the individual axes intersect between the focal zones and the creation surface, or beyond the focal zones, such that the beams originating from the sectors intersect to create a focal coverage zone which is off-axis relative to the plane of symmetry, or to the axis of symmetry, and situated at a distance from the focal planes, between the focal zones and the creation surface, or beyond the focal zones;

wherein the sectors of this creation surface are engendered either by rotation of $2\pi/N$ of the segments of concave curve around the axis of symmetry, or by translation of the segments of curve according to a direction perpendicular to the profile plane containing said segments of curve such that the sectors can create energy deposit zones with profiles corresponding to the focal coverage zones;

wherein the segments of curve of the creation surface extend in the profile plane on either side of the axis of symmetry, or of the plane of symmetry, by being separate to allow positioning of the focal coverage zone at a distance from the creation surface;

wherein each one of the plurality of ultrasound emitters is connected to its own signal generator;

wherein the ultrasound emitters are distributed according to several sectors perpendicular to the plane of symmetry; and wherein the ultrasound emitters of sectors in successive exposure phases are activated by signals delivered by the signal generator forming part of the control circuit to create energy deposit zones on either side of the plane of symmetry.

* * * * *